US008846066B2

(12) United States Patent
Kolodney et al.

(10) Patent No.: US 8,846,066 B2
(45) Date of Patent: *Sep. 30, 2014

(54) METHODS AND RELATED COMPOSITIONS FOR REDUCTION OF FAT AND SKIN TIGHTENING

(71) Applicants: Michael S. Kolodney, Santa Monica, CA (US); Adam M. Rotunda, Los Angeles, CA (US)

(72) Inventors: Michael S. Kolodney, Santa Monica, CA (US); Adam M. Rotunda, Los Angeles, CA (US)

(73) Assignees: The Regents of the University of California, Oakland, CA (US); Los Angeles Biomedical Research Institute at Harbor-UCLA Medical Center, Torrance, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/917,450

(22) Filed: Jun. 13, 2013

(65) Prior Publication Data

US 2014/0004206 A1 Jan. 2, 2014

Related U.S. Application Data

(63) Continuation of application No. 12/782,629, filed on May 18, 2010, now abandoned, which is a continuation of application No. 11/286,825, filed on Nov. 23, 2005, now abandoned, which is a continuation-in-part of application No. 11/134,727, filed on May 19, 2005, now Pat. No. 7,754,230, which is a continuation-in-part of application No. 11/054,171, filed on Feb. 8, 2005, now Pat. No. 7,622,130.

(60) Provisional application No. 60/572,879, filed on May 19, 2004.

(51) Int. Cl.
*A61K 8/02* (2006.01)
*A61K 31/575* (2006.01)
*A61K 8/63* (2006.01)
*A61K 31/185* (2006.01)
*A61K 47/24* (2006.01)
*A61K 31/685* (2006.01)
*A61K 9/00* (2006.01)
*A61Q 19/06* (2006.01)
*A61K 31/56* (2006.01)
*A61K 47/28* (2006.01)
*A61Q 19/08* (2006.01)
*A61K 35/12* (2006.01)

(52) U.S. Cl.
CPC .............. *A61K 31/575* (2013.01); *A61K 8/63* (2013.01); *A61K 31/185* (2013.01); *A61K 47/24* (2013.01); *A61K 31/685* (2013.01); *A61K 9/0019* (2013.01); *A61Q 19/06* (2013.01); *A61K 31/56* (2013.01); *A61K 47/28* (2013.01); *A61Q 19/08* (2013.01); *A61K 35/35* (2013.01); *A61K 2800/91* (2013.01)
USPC ........................................................ 424/401

(58) Field of Classification Search
USPC ............................................................ 424/401
See application file for complete search history.

(56) References Cited

U.S. PATENT DOCUMENTS

| | | | |
|---|---|---|---|
| 4,113,882 | A | 9/1978 | Okazaki et al. |
| 4,117,121 | A | 9/1978 | Gallo-Torres et al. |
| 4,158,707 | A | 6/1979 | Steffen et al. |
| 4,664,910 | A | 5/1987 | Caserio et al. |
| 4,681,876 | A | 7/1987 | Marples et al. |
| 4,851,435 | A | 7/1989 | Sauer et al. |
| 4,866,044 | A | 9/1989 | Sato et al. |
| 4,994,439 | A | 2/1991 | Longenecker et al. |
| 5,085,864 | A | 2/1992 | Cannon et al. |
| 5,288,498 | A | 2/1994 | Stanley et al. |
| 5,326,562 | A | 7/1994 | Scott |
| 5,344,822 | A | 9/1994 | Levine et al. |
| 5,371,104 | A | 12/1994 | Feigenbaum |
| 5,376,646 | A | 12/1994 | Pittrof et al. |
| 5,395,545 | A | 3/1995 | Fischer et al. |
| 5,506,218 | A | 4/1996 | Parker et al. |
| 5,603,932 | A | 2/1997 | Blaas et al. |

(Continued)

FOREIGN PATENT DOCUMENTS

| | | |
|---|---|---|
| CA | 2033725 | 5/2001 |
| CA | 2551474 | 7/2005 |

(Continued)

OTHER PUBLICATIONS

Zeghari N, Younsi M, Meyer L, Donner M, Drouin P, Ziegler O. Adipocyte and erythrocyte plasma membrane phospholipid composition and hyperinsulinemia: a study in nondiabetic and diabetic obese women. Int J Obes Relat Metab Disord. Dec. 2000;24(12):1600-7.*

(Continued)

*Primary Examiner* — Paul Zarek
(74) *Attorney, Agent, or Firm* — K&L Gates LLP; Louis C. Cullman; Michelle Glasky Bergman

(57) ABSTRACT

Compositions and methods useful in the reduction of localized fat deposits and tightening of loose skin in subjects in need thereof using pharmacologically active detergents are disclosed. The pharmacologically active detergent compositions can additionally include anti-inflammatory agents, analgesics, dispersion or anti-dispersion agents and pharmaceutically acceptable excipients. The pharmacologically active detergent compositions are useful for treating localized accumulations of fat including, for example, lower eyelid fat herniation, lipodystrophy and fat deposits associated with cellulite and do not require surgical procedures such as liposuction.

7 Claims, 9 Drawing Sheets

(56) References Cited

U.S. PATENT DOCUMENTS

| | | |
|---|---|---|
| 5,616,342 A | 4/1997 | Lyons |
| 5,674,855 A | 10/1997 | Levine et al. |
| 5,747,066 A | 5/1998 | Pittrof et al. |
| 5,759,445 A | 6/1998 | Yamamoto et al. |
| 5,849,883 A | 12/1998 | Boone et al. |
| 5,863,554 A | 1/1999 | Illum |
| 5,876,721 A | 3/1999 | Alexander et al. |
| 5,891,083 A | 4/1999 | Capella et al. |
| 5,914,390 A | 6/1999 | Nathan et al. |
| 5,942,248 A | 8/1999 | Barnwell |
| 5,952,313 A | 9/1999 | Carlson |
| 5,952,392 A | 9/1999 | Katz et al. |
| 6,025,396 A | 2/2000 | Kim et al. |
| 6,120,805 A | 9/2000 | Spenlehauer et al. |
| 6,197,327 B1 | 3/2001 | Harrison et al. |
| 6,221,378 B1 | 4/2001 | Modi |
| 6,225,343 B1 | 5/2001 | Behl et al. |
| 6,251,428 B1 | 6/2001 | Yoo |
| 6,255,502 B1 | 7/2001 | Penkler et al. |
| 6,294,192 B1 | 9/2001 | Patel et al. |
| 6,313,128 B1 | 11/2001 | Blanc-Ferras et al. |
| 6,315,984 B1 | 11/2001 | Modi |
| 6,342,489 B1 | 1/2002 | Palmieri et al. |
| 6,350,458 B1 | 2/2002 | Modi |
| 6,375,975 B1 | 4/2002 | Modi |
| 6,383,471 B1 | 5/2002 | Chen et al. |
| 6,416,779 B1 | 7/2002 | D'Augustine et al. |
| 6,417,179 B1 | 7/2002 | Burkhart et al. |
| 6,451,286 B1 | 9/2002 | Modi |
| 6,489,312 B1 | 12/2002 | Stogniew et al. |
| 6,537,561 B1 | 3/2003 | Fukui et al. |
| 6,544,972 B1 | 4/2003 | Steer et al. |
| 6,663,885 B1 | 12/2003 | Hager et al. |
| 6,713,470 B2 | 3/2004 | Jackson |
| 6,849,263 B2 | 2/2005 | Modi |
| 6,884,768 B2 | 4/2005 | Kimura et al. |
| 7,226,775 B2 | 6/2007 | Mapleson et al. |
| 7,303,768 B2 | 12/2007 | Yoo |
| 7,538,093 B2 | 5/2009 | Engler et al. |
| 7,622,130 B2 * | 11/2009 | Kolodney et al. ............ 424/401 |
| 7,754,230 B2 * | 7/2010 | Kolodney et al. ............ 424/401 |
| 8,101,593 B2 | 1/2012 | Hodge et al. |
| 8,298,556 B2 | 10/2012 | Kolodney et al. |
| 8,367,649 B2 | 2/2013 | Hodge et al. |
| 2001/0051595 A1 | 12/2001 | Lyons et al. |
| 2002/0028766 A1 | 3/2002 | Papadimitriou |
| 2002/0031558 A1 | 3/2002 | Yoo |
| 2002/0032159 A1 | 3/2002 | Maruyama et al. |
| 2002/0058010 A1 | 5/2002 | Picard-Lesboueyries et al. |
| 2002/0107291 A1 | 8/2002 | De Tommaso |
| 2002/0168402 A1 | 11/2002 | Kipp et al. |
| 2003/0027833 A1 | 2/2003 | Cleary et al. |
| 2003/0035831 A1 | 2/2003 | Modi |
| 2003/0054981 A1 | 3/2003 | Milton et al. |
| 2003/0064097 A1 | 4/2003 | Patel et al. |
| 2003/0072807 A1 | 4/2003 | Wong et al. |
| 2003/0077329 A1 | 4/2003 | Kipp et al. |
| 2003/0161886 A1 | 8/2003 | Dickinson et al. |
| 2003/0186933 A1 | 10/2003 | Yoo |
| 2003/0219472 A1 | 11/2003 | Pauletti et al. |
| 2004/0022862 A1 | 2/2004 | Kipp et al. |
| 2004/0038952 A1 | 2/2004 | Feher |
| 2004/0067919 A1 | 4/2004 | Jee |
| 2004/0096494 A1 | 5/2004 | Siekmann et al. |
| 2004/0101569 A1 | 5/2004 | Rang |
| 2004/0115255 A1 | 6/2004 | Leigh et al. |
| 2004/0141949 A1 | 7/2004 | Rosenthal et al. |
| 2004/0161407 A1 | 8/2004 | Kimura et al. |
| 2004/0201117 A1 | 10/2004 | Anderson |
| 2004/0213855 A1 | 10/2004 | Pettersson et al. |
| 2004/0220283 A1 | 11/2004 | Zhang et al. |
| 2005/0019404 A1 | 1/2005 | Sung et al. |
| 2005/0048126 A1 | 3/2005 | Rabinow et al. |
| 2005/0079228 A1 | 4/2005 | Jaiswal et al. |
| 2005/0089555 A1 | 4/2005 | Boderke et al. |
| 2005/0123582 A1 | 6/2005 | Sung et al. |
| 2005/0143347 A1 * | 6/2005 | Boderke et al. ............... 514/78 |
| 2005/0158408 A1 | 7/2005 | Yoo |
| 2005/0163821 A1 | 7/2005 | Sung et al. |
| 2005/0261258 A1 | 11/2005 | Kolodney et al. |
| 2005/0266065 A1 | 12/2005 | Perrier et al. |
| 2005/0287199 A1 | 12/2005 | Denney et al. |
| 2006/0074057 A1 | 4/2006 | Marchewitz |
| 2006/0127468 A1 | 6/2006 | Kolodney et al. |
| 2006/0154906 A1 | 7/2006 | Kolodney et al. |
| 2006/0222673 A1 | 10/2006 | Chern et al. |
| 2006/0222695 A1 | 10/2006 | Zadini et al. |
| 2008/0318870 A1 | 12/2008 | Moriarty et al. |
| 2009/0270642 A1 | 10/2009 | Prasad et al. |
| 2009/0275545 A1 | 11/2009 | Boderke et al. |
| 2010/0048527 A1 | 2/2010 | Kolodney et al. |
| 2010/0292650 A1 | 11/2010 | Kolodney et al. |
| 2011/0002896 A1 | 1/2011 | Kolodney et al. |
| 2012/0237492 A1 | 9/2012 | Walker |
| 2012/0258943 A1 | 10/2012 | Hodge et al. |
| 2013/0190282 A1 | 7/2013 | Hodge et al. |

FOREIGN PATENT DOCUMENTS

| | | |
|---|---|---|
| EP | 0 208 519 | 1/1987 |
| EP | 0 426 029 | 5/1991 |
| EP | 0 439 042 | 6/1995 |
| EP | 0 439 513 | 3/1996 |
| EP | 1 111 390 | 6/2001 |
| EP | 0 730 860 | 1/2002 |
| EP | 0 806 940 | 4/2003 |
| EP | 1 005 324 | 3/2005 |
| JP | 61-158995 | 7/1986 |
| JP | 03-048622 | 3/1991 |
| JP | 04-235918 | 8/1992 |
| JP | 11-240835 | 9/1999 |
| JP | 2007-515439 | 6/2007 |
| JP | 2007-515494 | 6/2007 |
| JP | 2007-538104 | 12/2007 |
| WO | WO-90/12583 | 11/1990 |
| WO | WO-93/05811 | 4/1993 |
| WO | WO-94/04177 | 3/1994 |
| WO | WO-99/15152 | 4/1999 |
| WO | WO-00/13029 | 3/2000 |
| WO | WO-02/058610 | 8/2002 |
| WO | WO-03/018134 | 3/2003 |
| WO | WO-03/082340 | 10/2003 |
| WO | WO-03/094894 | 11/2003 |
| WO | WO-2004/010941 | 2/2004 |
| WO | WO-2004/039326 | 5/2004 |
| WO | WO-2005/020894 | 3/2005 |
| WO | WO-2005/061004 | 7/2005 |
| WO | WO-2005/063169 | 7/2005 |
| WO | WO-2005/063205 | 7/2005 |
| WO | WO-2005/112942 | 12/2005 |
| WO | WO-2005/117832 | 12/2005 |
| WO | WO-2005/117900 | 12/2005 |
| WO | WO-2006/007675 | 1/2006 |
| WO | WO-2006/133160 | 12/2006 |
| WO | WO-2011/075701 | 6/2011 |

OTHER PUBLICATIONS

U.S. Appl. No. 11/710,601, filed Feb. 23, 2007, Burkhart et al.
U.S. Appl. No. 12/062,445, filed Apr. 3, 2008, Kolodney et al.
U.S. Appl. No. 12/397,229, filed Mar. 3, 2009, Hodge et al.
U.S. Appl. No. 13/753,366, filed Jan. 29, 2013, Hodge et al.
Author Unknown. Deoxycholic acid, Product Information, SIGMA, Nov. 2002.
Author Unknown. Health Alert: Lipostabil. http://kyw.com/health/local.sub.--story.sub.--336152706.html, Dec. 2, 2002.
Author Unknown. Learn about lecithins. Oxford, CT: American Lecithin Company (2003).
Author Unknown. Lipostabil. Rhone-Polenc Rorer. Cologne, West Germany: Natterman International GmbH (1990).
Author Unknown. Lose those love handles, A CBS HealthWatch Special Report http://cbsnewyork.com/healthwatch/local.sub.--story.sub.--329141707.html, Nov. 25, 2002.

(56) References Cited

OTHER PUBLICATIONS

Author Unknown. Love handles can be shrunk without surgery http://www.macleans.ca/topstories/health/article.jsp?content=20040225.sub-.--090843.sub.--4800, Feb. 25, 2004.

Aasadi et al. Mesoplasty: A new approach to non-surgical liposculpture. Plastic Surgery 2004, Oct. 10, 2004, Philadelphia, PA.

Ablon et al. Treatment of Lower Eyelid Fat Pads Using Phosphatidylcholine: Clinical Trial and Review, Dermatol. Surg. (2004) 30(3):422-427.

Alkan-Onyuksel et al. A mixed micellar formulation suitable for the parenteral administration of taxol. Pharm Res (1994) 11(2):206-212.

Almgren M. Mixed micelles and other structures in the solubilization of bilayer lipid membranes by surfactants. Biochim Biophys Acta (2000)1508:146-163.

ASAPS. American Society for Aesthetic Plastic Surgery. Lipoplasty (liposuction) without surgery?, Oct. 2002.

Banerjee et al. Differential solubilization of lipids along with membrane proteins by different classes of detergents. Chem Phys Lipids (1995) 77:65-78.

Bates B. Fat dissolving substance injects CCs of controversy. Skin and Allergy News (2003) 34(2).

Bayer Press Release. First Patients enrolled in EU Phase III Clinical Development Program to evaluate ATX-101 for reduction of Submental Fat. (2008).

Bellman B. Phosphatidylcholine reaction. Skin and Allergy News (2003) 34(4).

Bryant R. Controversial mesotherapy: could it be the next botox. Dermatology Times (2004) 1-2.

Buko et al. Hepatic and pancreatic effects of polyenoylphosphatidylcholine in rats with alloxan-induced diabetes. Cell Biochem Function (1996)14:131-137.

Canty et al. Lecithin and choline: research update on health and nutrition. Fort Wayne, IN: Central Soya Company, Inc. (1998).

Chalmers K. Fat loss a needle away. http://surgerynews.neUnews/0204/meso020402.htm, Feb. 1, 2004.

Davidson et al. Limitations of phosphatidylcholine/deoxycholate mixtures for the analysis of phospholipase $A_2$ inhibition and activation: illustration with annexins. Biochimica et Biophysica Acta, (1992) 1127(3):270-276.

Duncan et al. Injectable therapies for localized fat loss: state of the art., Clinics in Plastic Surgery, LNKDpubmed:21824545, (2011) 38(3): 489-501.

Duncan et al. Lipodissolve for Subcutaneous Fat Reduction and Skin Retraction, Aesthetic Surgery Journal (2005) 25(5):530-543.

Durr et al. Investigation on mixed micelle and liposome preparations for parental use on soya phosphatidylcholine. Eur J Pharm Biopharm (1994) 40(3):147-156.

Ebihara et al. Effect of benzyl alcohol on lipid bilayers. A comparisons of bilayer systems. Biophys J (1979) 28:185-196.

Engelke et al. Effect of inhalation anaesthetics on the phase behaviour, permeability and order of phosphatidylcholine bilayers. Biophys Chem (1997)67:127-138.

FDA news release: FDA issues warning letters for drugs promoted in fat elimination procedure (2010) Retrieved from the Internet: URL:http://www.fda.gov/NewsEvents/Newsroom/PressAnnouncements/ucm207453.htm [retrieved on Oct. 18, 2011].

Goldman et al. Cecil Textbook of Medicine. St. Louis, MO: W.B. Saunders Co. (2001)21(1):821-833.

Gordon et al. The increase in bilayer fluidity of rat liver plasma membranes achieved by the local anesthetic benzyl alcohol affects the activity of intrinsic membrane enzymes. J Biol Chem (1980) 255(10):4519-4527.

Gustafson et al. Influence of organic solvent mixtures on biological membranes. Br J Ind Med (1985) 42:591-595.

Hammad et al. Increasing drug solubility by means of bile salt-phosphatidylcholine-based mixed micelles. Eur J Pharm Biopharm (1998) 46:361-367.

Hasengschwandtner F. Phosphatidylcholine treatment to induce lipolysis. Journal of Cosmetic Dermatology (2005) 4:308-313.

Heerklotz et al. Correlation of membrane/water partition coefficients of detergents with the critical micelle concentration. Biophys J (2000) 78:2435-2440.

Hexsel et al. Phosphatidylcholine in the treatment of localized fat, J. Drugs Dermatol. (2003) 2(5):511-518.

Hofmann et al. Bile acid solubility and precipitation in vitro and in vivo: the role of conjugation, pH, and $Ca^{2+}$ ions, Journal of Lipid Research (1992) 33:617-626.

Igimi et al. pH-Solubility relations of chenodeoxycholic and ursodeoxycholic acids: physical-chemical basis for dissimilar solution and membrane phenomena, Journal of Lipid Research (1980) 21:72-90.

Jones MN. Surfactants in membrane solubilisation. Int J Pharm (1999)177:137-59.

Kawanaka et al., Kan Tan Sui, (2002) 44(4): 521-526 with partial translation.

Kern et al. Regulation of Lipoprotein Lipase Immunoreactive Mass in Isolated Human Adipocytes. J. Clin. Invest. (1988) 81:398-406.

Klein et al. A New Method to Quantify the Effect After Subcutaneous Injection of Lipolytic Substances. Aesth Plast Surg. (2008) 32:667-672.

Kolonin et al. Reversal of obesity by targeted ablation of adipose tissue. Nature Medicine, Nature Publishing Group (2004) 10(6): 625-632.

Kythera Biopharmaceuticals: Evaluation of safety and efficacy of ATX-101 in the reduction of submental fat (2011) Retrieved from the Internet: URL:http://clinicaltrials.gov/ct2/show/NCT01305577, [retrieved on Oct. 18, 2011].

Kythera Newsroom. Two Phase 2 studies with ATX-101—study results demonstrated statistically significant reduction in patients' unwanted submental fat. Kythera Biopharmaceuticals, Inc. (2009) 1-2.

Landman B. Beyond Botox. Cosmetic Surgery Guide 2003 http://newyorkmetro.com/nymetro/health/bestdoctors/cosmeticsurgery/2003/n-.sub.--9281/index.html.

Lester et al. Action of organic solvents on protein kinase C. Eur J Pharmacol (1991) 206:301-308.

Lichtenberg D. Characterization of the solubilization of lipid bilayers by surfactants. Biochim Biophys Acta (1985) 821:470-478.

Lichtenberg et al. Solubilization of phospholipids by detergents. Structural and kinetic aspects. Biochim Biophys Acta (1983) 737:285-304.

Lichtenberg et al. Structural and kinetic studies on the solubilization of lecithin by sodium deoxycholate. Biochemistry (1979) 18(16):3517-3525.

Lieber et al. Phosphatidylcholine protects against fibrosis and cirrhosis in the baboon. Gastroenterology (1994)106:152-159.

McCaslin. Detergent Properties, Encyclopedia of Biological Chemistry. (2004) 1:577-581.

Moy LS. Phosphatidylcholine injections: A study measuring decreased subcutaneous fat thickness. Combined Annual Meeting of the American Society for Dermatologic Surgery and the American Society of Mohs Micrographic Surgery and Cutaneous Oncology, San Diego, CA Sep. 30-Oct. 3, 2004.

Milovic et al. Effects of deoxycholate on human colon cancer cells: apoptosis or proliferation. European Journal of Clinical Investigation. (2002) 32(1):29-34.

Parnham et al. Phospholipids and liposomes—safety for cosmetical and pharmaceutical use. Nattermann Phospholipid GmbH Scientific Publication (1995)No. 2:1-56.

Powell et al. Bile acid hydrophobicity is correlated with induction of apoptosis and/or growth arrest in HCT116 cells. Biochem. J. (2001) 356:481-486.

Rittes PG. The use of phosphatidylcholine for correction of localized fat deposits, Aesthetic Plast. Surg. (2003) 27(4):315-318.

Rittes PG. The use of phosphatidylcholine for correction of lower lid bulging due to prominent fat pads. Dermatol Surg (2001) 27:391-392.

Rosenbaum M. An exploratory investigation of the morphology and biochemistry of cellulite, Annual Meeting of American Society for Aesthetic Surgery (1997)101(7):1934-1939.

Rossi et al. Cellulite: A review. JEADV (2000)14:251-262.

(56) References Cited

OTHER PUBLICATIONS

Rotunda et al. Lipomas treated with subcutaneous deoxycholate injections. J. Am. Acad. Dermatol., (2005)973-978.

Rotunda et al. Mesotherapy and Phosphatidylcholine Injections: Historical Clarification and Review Dermatologic Surgery (2006) 32: 465-480.

Rotunda et al. Detergent effects of sodium deoxycholate are a major feature of injectable phosphatidylcholine. American Society for Dermatologic Surgery, New Orleans, LA, Oct. 11, 2003.

Rotunda et al. Detergent Effects of Sodium Deoxycholate Are a Major Feature of an Injectable Phosphatidylcholine Formulation Used for Localized Fat Dissolution, Dermatol. Surg. (2004), 30(7):1001-1008.

Rotunda et al. Randomized Double-Blind Clinical Trial of Subcutaneously Injected Deoxycholate Versus a Phosphatidylcholine-Deoxycholate Combination for the Reduction of Submental Fat. Dermatol Surg. (2009) 35:792-803.

Sager S. New fat removal technique getting raves: Is it safe? Does it work? http://abclocal.go.com/wabc/news/wabc.sub.--020703.sub.--mesotherap-y.html, Feb. 7, 2003.

Salti et al. Phosphatidylcholine and Sodium Deoxycholate in the Treatment of Localized Fat: A Double-Blind, Randomized Study. Dermatol Surg. (2008)34:60-66.

Schuck et al. Resistance of cell membranes to different detergents. Proc Natl Acad Sci (2003) 100(10):5795-5800.

Sergio M. Traitment mesotherapique das xanthelasmas a la phophatidilcoline polyinsaturee. Dermatologie (2009) 364-365.

Serra M. Subcutaneous infiltration with phosphatidylcholine solution for treatment of buffalo hump and fatty pads. 3rd Int'l workshop on adverse drug reactions and lipodystrophy in HIV, Athens, Oct. 2001, 115.

SIGMA: Rifa Buffer, 2003, retrieved from the internet: URL:http://www.sigmaaldrich.com/etc/medialib/docs/Sigma/Bulletin/r0278bul.Par.0001.File.tmp/r0278bul.pdf.

Singer et al. The fluid mosaic model of the structure of cell membranes. Science (1972) 175:720-731.

Small D.M. Size and structure of bile salt micelles. Molecular Association in Biological and Related Systems Chapter 4. (1968) 31-52.

Teelmann et al. Preclinical safety evaluation of intravenously administered mixed micelles. Arzneimittelforschung (1984)34:1517-1523.

Toyama M. Next-Gen Liposuction. http://www.time.com/time/europe/forecast2003/html/liposuction.html, Dec. 8, 2002.

Victor S. Phosphatidylcholine works. Skin and Allergy News (2003) 34.

Womack et al. Detergent effects on enzyme activity and solubilization of lipid bilayer membranes. Biochim Biophys Acta (1983)733:210-215.

Young, VL. Lipostabil: The effect of phosphatidylcholine on subcutaneous fat. Aesthetic Surg J (2003)23:413-417.

Duncan et al., "Fat Reduction Using Phosphatidylcholine/Sodium Deoxycholate Injections: Standard of Practice", Aesthetic Plastic Surgery, 2008, 32(6):858-872.

Extended European Search Report for Appl. No. 12747416.1, dated Jun. 10, 2014.

Hutchinson, ABC News Medical Unit: "Docs Question Bayer's Injection for Dissolving Double Chin", 2011, Retrieved from Internet: URL:http://abcnews.go.com/Health/WellnessNews/bayer-tests-fat-loss-injection-double-chin/story?id=12600333, [retrieved on May 22, 2014].

Japanese Office Action for Appl. No. 2013-034203, mailed Apr. 17, 2014.

\* cited by examiner

FIG. 9
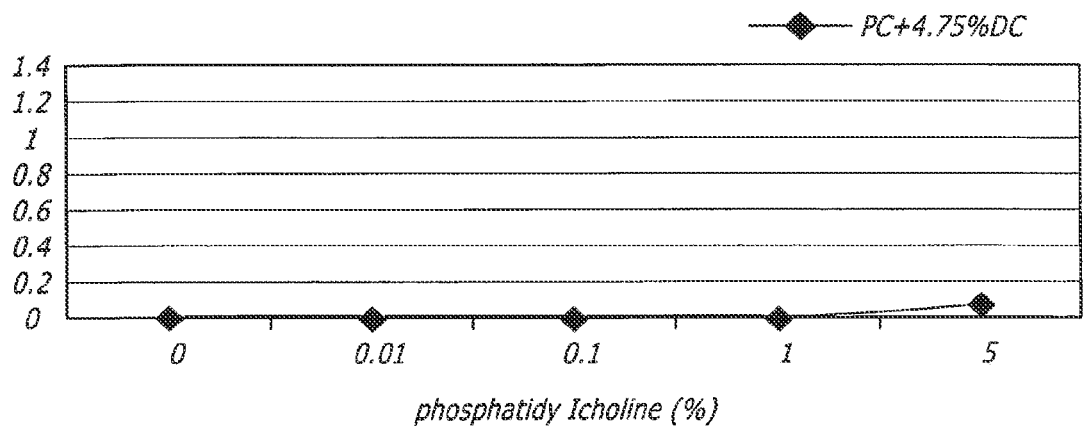
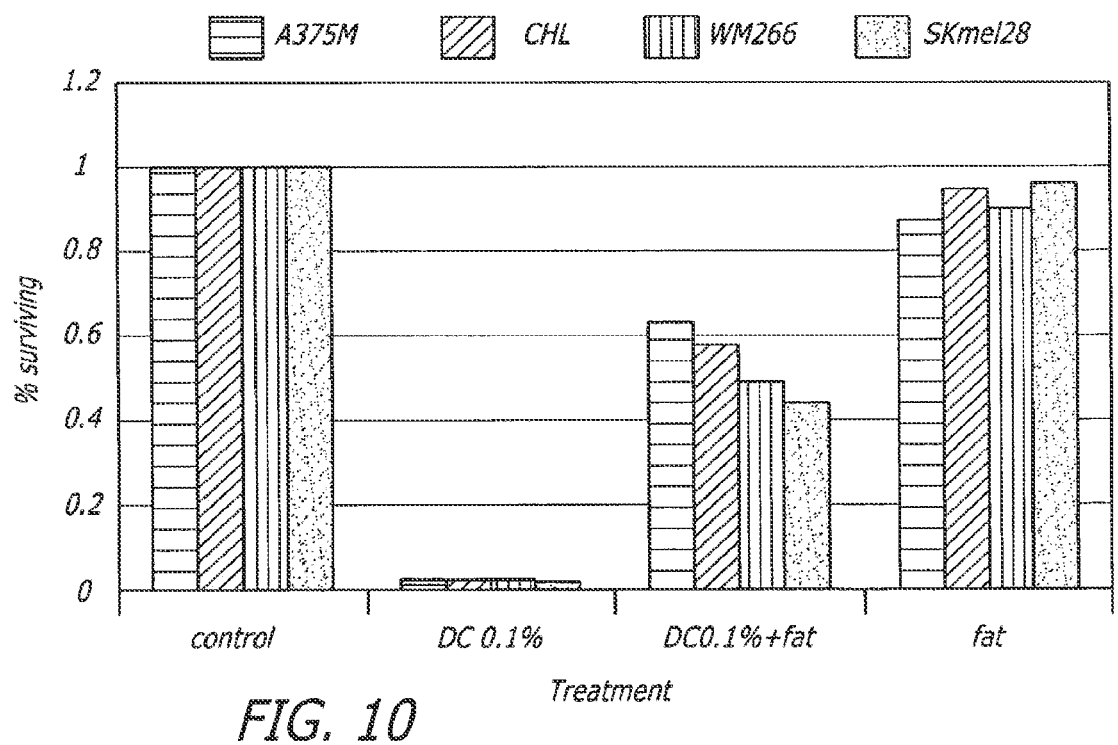
FIG. 10

METHODS AND RELATED COMPOSITIONS FOR REDUCTION OF FAT AND SKIN TIGHTENING

CROSS-REFERENCE

This application is a continuation of Ser. No. 12/782,629, filed May 18, 2010, which is a continuation of Ser. No. 11/286,825, filed Nov. 23, 2005, now abandoned, which is a continuation-in-part application of Ser. No. 11/134,727, filed May, 19, 2005, now U.S. Pat. No. 7,754,130, which is a continuation-in-part application of Ser. No. 11/054,171, filed Feb. 8, 2005, now U.S. Pat. No. 7,622,130, which claims priority to U.S. Provisional Application Ser. No. 60/572,879 filed May 19, 2004, all of which are incorporated herein by reference in their entirety.

BACKGROUND OF THE INVENTION

Surgical and non-surgical procedures for improving appearance have increased in prevalence as populations age and gain weight. Liposuction is a popular cosmetic surgery procedure and involves the surgical removal of fat deposits using suction and optionally assisted by solutions to assist in fat removal. Liposuction is a surgical procedure that removes fat through an incision in the skin through which a cannula is inserted. The cannula is connected to a suction source and the unwanted fat is aspirated through the cannula and discarded. Liposuction is performed under general or local anesthesia, depending on the amount and location of the fat to be removed. However, liposuction and other surgical methods of fat removal are associated with significant adverse events including temporary bruising, swelling, numbness, soreness and burning sensation, risk of infection, pigmentation changes, the formation of fat clots or blood clots which can migrate to the lungs and cause death, excessive fluid loss, which can lead to shock or fluid accumulation that must be drained, friction burns or other damage to the skin or nerves or perforation injury to the vital organs. Additionally, liposuction requires a recovery time of one to two weeks wherein the patient cannot work or perform certain daily activities. Moreover, because surgical procedures such as liposuction require local and occasionally general anesthesia, significant anesthesia-related risks are associated with surgical fat removal. Furthermore, liposuction and other drastic weight loss methods may result in loose skin.

Therefore it would be desirable to have compositions and methods for removing localized fat accumulations that does not require surgery or prolonged recovery time as well as for tightening loose skin.

SUMMARY OF THE INVENTION

The present invention provides compositions, methods, and kits for reducing subcutaneous fat deposits as well as tightening loose skin.

In one aspect, the compositions herein are in a solution. Preferably the solution is aqueous.

In one embodiment, the present invention relates to a solution for subcutaneous injection comprising: (i) a therapeutically effective amount of one or more pharmacologically active detergents, or bile acid(s) and/or bile salt(s), or deoxycholic acid or a salt thereof, or sodium deoxycholate; (ii) a pharmaceutical, veterinary, or cosmetic excipient; and (iii) optionally a lipid, wherein the ratio of the lipid and bile acid or bile salt is less than 1% w/w and wherein the solution does not include lipase or colipase.

In some embodiments, the above solution can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents.

In some embodiments, a solution is in a container that contains up to 500 mL of solution. Such container can be a syringe or syringe-loadable container.

In some embodiments, a solution comprises a bile acid selected from the group consisting of: deoxycholic acid, cholic acid, chenodeoxycholic acid, 7-alpha-dehydroxylate chenodeoxycholic acid, lithocholic acid, ursodeoxycholic acid, dihydroxytaurin acid, trihydroxytaurine acid, and glycine conjugates of any of the above.

In some embodiments, a solution comprises a bile salt wherein the salt comprises a cation selected from the group consisting of sodium ($Na^+$), potassium ($K^+$) lithium ($Li^+$), magnesium ($Mg^{2+}$), calcium ($Ca^{2+}$), barium ($Ba^{2+}$), strontium ($Sr^{2+}$), and ammonium ($NH^{4+}$). Preferably, when the above solution comprises a bile salt, the bile salt is sodium deoxycholate.

In some embodiments, a solution comprises a bile salt that includes an alkali metal or an alkaline earth metal. Preferably an alkali metal is selected from the group consisting of alkali metal is sodium ($Na^+$), potassium ($K^+$), and lithium ($Li^+$). Preferably, an alkaline earth metal is selected from the group consisting of magnesium ($Mg^{2+}$), calcium ($Ca^{2+}$), barium ($Ba^{2+}$), and strontium ($Sr^{2+}$).

The compositions (e.g., solutions) include a therapeutically effective amount of the pharmacological detergents (e.g., bile acid(s) and/or bile salt(s). Such therapeutically effective amounts are effective to reduce a subcutaneous fat deposit or tighten a region of loose skin.

The bile acid(s) or bile salt(s) in a solution of the invention can be at a concentration of about 0.001 to 10, 0.01 to 5, or 0.1 to 2% w/w, w/v, or v/v. Preferably, the bile acid(s) or bile salt(s) in the above solution can be at a concentration of about 0.1-5 w/w or more preferably about 1% w/w.

In some embodiments, the solutions herein include no lipids, phospholipids, or phosphatidylcholine. In some embodiments, the solutions herein include up to 5% w/w, w/v, or v/v lipids, phospholipids, or phosphatidylcholine.

In one aspect, the present invention relates to methods for reducing the appearance of a skin condition in a skin region of a subject. Such methods comprise the step of: administering locally to said skin region a composition comprising: (i) a skin-tightening effective amount of one or more pharmacologically active detergents, or bile acid(s) and/or bile salt(s), or deoxycholic acid or a salt thereof, or sodium deoxycholate, (ii) a pharmaceutical, veterinary, or cosmetic excipient, and (iii) optionally a lipid.

In some embodiments, the administering step involves delivering the compositions herein via a subcutaneous or transdermal injection.

In some embodiments, the administering step involves delivering the compositions herein via a dermal patch, a pump, or subdermal depot.

In some embodiments, the administering step involves delivering the compositions herein topically or subcutaneously.

In some embodiments, the skin condition being treated or ameliorated is selected from the group consisting of: loose skin, skin aging, irregularities of the skin, and wrinkles.

In some embodiments, the region of skin being treated is under eye, under chin, under arm, buttock, cheek, brow, calf, back, thigh, ankle, or stomach.

In some embodiments, the compositions used for reducing the appearance of a skin condition in a skin region are formulation into a skin tightening solution.

Such skin tightening solution can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents.

In some embodiments, the skin tightening solution is in a container that contains up to 500 mL of solution. Such container can be a syringe or syringe-loadable container.

In some embodiments, the skin tightening solution comprises a bile acid selected from the group consisting of: deoxycholic acid, cholic acid, chenodeoxycholic acid, 7-alpha-dehydroxylate chenodeoxycholic acid, lithocholic acid, ursodeoxycholic acid, dihydroxytaurin acid, trihydroxytaurine acid, and glycine conjugates of any of the above.

In some embodiments, a solution comprises a bile salt wherein the salt comprises a cation selected from the group consisting of sodium ($Na^+$), potassium ($K^+$), lithium ($Li^+$), magnesium ($Mg^{2+}$), calcium ($Ca^{2+}$), barium ($Ba^{2+}$), strontium ($Sr^{2+}$), and ammonium ($NH^{4+}$). Preferably, when the above solution comprises a bile salt, the bile salt is sodium deoxycholate.

In some embodiments, the skin tightening solution comprises a bile salt that includes an alkali metal or an alkaline earth metal. Preferably an alkali metal is selected from the group consisting of alkali metal is sodium ($Na^+$), potassium ($K^+$), and lithium ($Li^+$). Preferably, an alkaline earth metal is selected from the group consisting of magnesium ($Mg^{2+}$), calcium ($Ca^{2+}$), barium ($Ba^{2+}$), and strontium ($Sr^{2+}$).

In some embodiments, the skin tightening solution includes a therapeutically effective amount of the pharmacological detergents (e.g., bile acid(s) and/or bile salt(s)). Such therapeutically effective amount is effective to tighten a loose skin region.

In some embodiments, the skin tightening solution comprises one or more pharmacologically active detergents (e.g., bile acid(s) and/or bile salt(s), such as sodium deoxycholate) at a concentration of about 0.001 to 10, 0.01 to 5, or 0.1 to 2% w/w, w/v, or v/v. Preferably, the one or more pharmacologically active detergents in the skin tightening solution is at a concentration of about 0.1-5 w/w, or more preferably about 1% w/w.

In some embodiments, the skin tightening solution comprises up to 100, 50, 20, 10, 5, 2, 1, 0.5, 0.2, 0.05, 0.02, or 0.01 grams of the one or more detergents, bile acids and/or bile salts, deoxycholic acid or salts thereof or sodium deoxycholate.

In some embodiments, the skin tightening solution includes no lipids, phospholipids, or phosphatidylcholine. In some embodiments, the solutions herein include up to 5% w/w, w/v, or v/v lipids, phospholipids, or phosphatidylcholine.

In one aspect, the present invention relates to methods for reducing a subcutaneous fat deposit in a subject. Such methods comprise the step of administering locally to a subcutaneous fat deposit in the subject a composition comprising: (i) a fat-dissolving effective amount of one or more pharmacologically active detergents, or bile acid(s) and/or bile salt(s), or deoxycholic acid or a salt thereof, or sodium deoxycholate; (ii) a pharmaceutical, veterinary, or cosmetic excipient; and (iii) optionally a lipid, wherein the ratio of the lipid and bile acid or bile salt is up to 1% w/w and wherein the composition does not include lipase or colipase.

In some embodiments, the fat deposit is associated with a condition selected from the group consisting of obesity, fat redistribution syndrome, eyelid fat herniation, lipomas, Dercum's disease, lipodystrophy, buffalo hump lipodystrophy, dorsocervical fat, visceral adiposity, breast enlargement, hyperadiposity, diffused body fat around trunk and arms, and fat deposits associated with cellulite.

In some embodiments, the detergent comprises a bile acid selected from the group consisting of deoxycholic acid, cholic acid, chenodeoxycholic acid, 7-alpha-dehydroxylate chenodeoxycholic acid, lithocholic acid, ursodeoxycholic acid, dihydroxytaurin acid, trihydroxytaurine acid, and glycine conjugates of any of the above.

In some embodiments, the detergent comprises a bile salt that includes a cation selected from the group consisting of sodium ($Na^+$), potassium ($K^+$), lithium ($Li^+$), magnesium ($Mg^{2+}$), calcium ($Ca^{2+}$), barium ($Ba^{2+}$), strontium ($Sr^{2+}$), and ammonium ($NH^{4+}$).

In some embodiments, the detergent comprises a bile salt with a cation that is an alkali metal or an alkaline earth metal. Preferably, the alkali metal is sodium ($Na^+$), potassium ($K^+$), or lithium ($Li^+$) and the alkaline earth metal is magnesium ($Mg^{2+}$), calcium ($Ca^{2+}$), barium ($Ba^{2+}$), or strontium ($Sr^{2+}$). More preferably, the bile salt is sodium deoxycholate.

In some embodiments, the above method does not include performing surgery on said subject.

In some embodiments, the administration step involves administering locally (e.g., subcutaneously or subdermally) to a region under eye, under chin, under arm, buttock, calf, back, thigh, or stomach of said subject. The administration can be made by a subcutaneous or transdermal injection.

The subject being treated by the compositions herein can be a human or a domesticated animal such as a cat, dog, or horse. In some embodiments, the subject being treated is a human HIV patient. Such patient can be undergoing a HIV protease treatment or experiencing or susceptible to experiencing lipodystriphy.

In some embodiments, the composition (e.g., solution or aqueous solution) being administered includes up to 5% w/w, w/v or v/v lipids, phospholipids, or phosphatidylcholine. Preferably, the composition (e.g., solution or aqueous solution) being administered includes up to 5% w/w phosphatidylcholine.

In some embodiments, the composition (e.g., solution or aqueous solution) being administered comprises 0.001 to 10, 0.01 to 5, or 0.1 to 2% w/w, w/v, or v/v detergent(s) or bile acid(s) and/or bile salt(s). More preferably a composition (e.g., solution herein) comprises about 0.1-5 w/w or more preferably about 1% w/w bile salts such as sodium deoxycholate.

Preferably, the compositions once administered are not removed from the subject. Furthermore, the compositions herein are preferably administered without a surgical procedure (e.g., liposuction).

In some embodiments, the fat dissolving solution comprises up to 100, 50, 20, 10, 5, 2, 1, 0.5, 0.2, 0.05, 0.02, or 0.01 grams of the one or more detergents, bile acids and/or bile salts, deoxycholic acid or salts thereof or sodium deoxycholate.

In one aspect, the present invention relates to a syringe loadable container comprising: (i) a fat-dissolving or skin-tightening effective amount of one or more pharmacologically active detergents, or bile acid(s) and/or bile salt(s), or deoxycholic acid or a salt thereof, or sodium deoxycholate;

(ii) a pharmaceutical, veterinary, or cosmetic excipient; and (iii) optionally a lipid wherein the ratio of said bile acid or bile salt to said lipid is greater than 1% w/w and wherein the solution does not contain lipase or colipase.

Preferably, the one or more detergents herein comprise sodium deoxycholate.

Preferably the container contains up to 500, 200, 100, 50, 20, 10, 5, 2, or 1 mL of a solution that is sterile.

In some embodiments, the solution comprises an organic solvent, or more preferably benzyl alcohol.

In some embodiments, the solution comprises 0.001 to 10, 0.01 to 5, or 0.1 to 2% w/w, w/v, or v/v detergent(s) or bile acid(s) and/or bile salt(s). More preferably the solution comprises about 0.1-5% w/w or more preferably about 1% w/w bile salts such as sodium deoxycholate.

In some embodiments, the solution comprises up to 100, 50, 20, 10, 5, 2, 1, 0.5, 0.2, 0.05, 0.02, or 0.01 grams of the one or more detergents, bile acids and/or bile salts, deoxycholic acid or salts thereof or sodium deoxycholate.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 9 depicts effects of addition of phosphatidylcholine to 4.75% sodium deoxycholate solutions on viable adipocytes.

FIG. 10 depicts inhibition of adipolysis by pre-incubation with human lipoma fat.

DETAILED DESCRIPTION OF THE INVENTION

Figure 1:
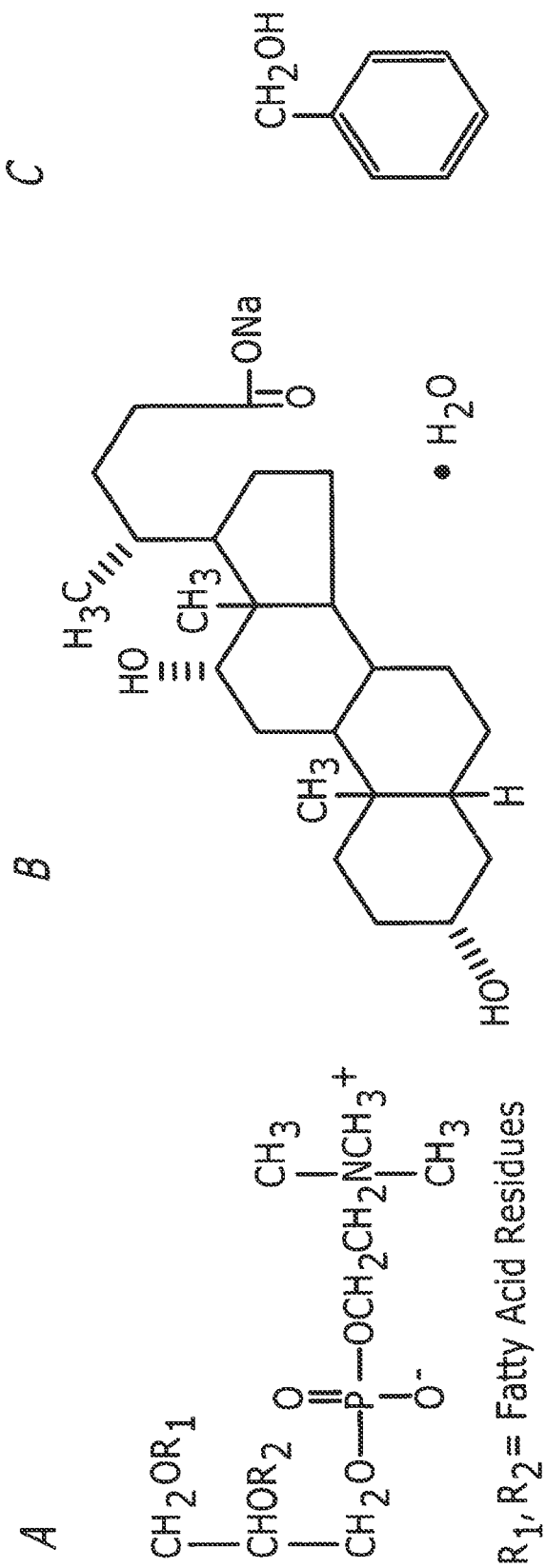
FIG. 1 depicts the molecular structure of (a) phosphatidylcholine (b) sodium deoxycholate and (c) benzyl alcohol.

The present invention addresses problems of localized fat accumulation and loose skin in animals, such as humans. In one aspect, the present invention provides compositions for reducing fat deposits and tightening skin. Such compositions comprise, consist essentially of, or consist of one or more pharmacologically active detergents, more preferably bile acids or bile salts, more preferably deoxycholic acid or a salt thereof, or more preferably sodium deoxycholate. The amount of such detergent(s) in the composition is an effective amount to dissolve or reduce a subdermal fat deposit or to tighten loose skin. Such effective amount will depend, in part, on the location of target site, size of target site, length of treatment, etc. In some of the embodiments, a composition includes at least 2, 3, 4, 5, 6, 7, 8, 9, or 10 pharmacologically active detergents.

Pharmacologically active and biologically compatible detergents include, but are not limited to, lipophilic detergents (whether ionic or non-ionic), hydrophilic detergents (whether ionic or non-ionic), ionic detergents, non-ionic detergents, zwitterionic detergents, glycerides, bile acids and bile salts.

Non-limiting examples of lipophilic detergents include, inter alia, alcohols, polyoxyethylene alkylethers, fatty acids, bile acids, glycerol fatty acid esters, acetylated glycerol fatty acid esters, lower alcohol fatty acids esters, polyethylene glycol fatty acid esters, polyethylene glycol glycerol fatty acid esters, polypropylene glycol fatty acid esters, polyoxyethylene glycerides, lactic acid derivatives of mono/diglycerides, propylene glycol diglycerides, sorbitan fatty acid esters, polyoxyethylene sorbitan fatty acid esters, polyoxyethylene-polyoxypropylene block copolymers, transesterified vegetable oils, sterols, sterol derivatives, sugar esters, sugar ethers, sucroglycerides, polyoxyethylene vegetable oils, polyoxyethylene hydrogenated vegetable oils, reaction mixtures of polyols and at least one member of the group consisting of fatty acids, glycerides, vegetable oils, hydrogenated vegetable oils, and sterols, and mixtures thereof.

Non-limiting examples of non-ionic lipophilic detergents include, inter alia, alkylglucosides, alkylmaltosides, alkylthioglucosides, lauryl macrogolglycerides, polyoxyethylene alkyl ethers, polyoxyethylene alkylphenols, polyethylene glycol fatty acids esters, polyethylene glycol glycerol fatty acid esters, polyoxyethylene sorbitan fatty acid esters, polyoxyethylene-polyoxypropylene block copolymers, polyglycerol fatty acid esters, polyoxyethylene glycerides, polyoxyethylene sterols, derivatives, and analogues thereof, polyoxyethylene vegetable oils, polyoxyethylene hydrogenated vegetable oils, reaction mixtures of polyols and at least one member of the group consisting of fatty acids, glycerides, vegetable oils, hydrogenated vegetable oils, and sterols, tocopherol polyethylene glycol succinates, sugar esters, sugar ethers, sucroglycerides, and mixtures thereof.

Non-limiting examples of ionic hydrophilic detergents include, inter alia, alkyl ammonium salts, bile acids and bile salts, analogues, and derivatives thereof, fatty acid derivatives of amino acids, carnitines, oligopeptides, and polypeptides, glyceride derivatives of amino acids, oligopeptides, and polypeptides, acyl lactylates, mono-, diacetylated tartaric acid esters of mono-, diglycerides, succinoylated monoglycerides, citric acid esters of mono-, diglycerides, alginate salts, propylene glycol alginate, lecithins and hydrogenated lecithins, lysolecithin and hydrogenated lysolecithins, lysophospholipids and derivatives thereof, phospholipids and derivatives thereof, salts of alkylsulphates, salts of fatty acids, sodium docusate, and mixtures thereof.

Non-limiting examples of ionic detergents include, but not limited to, cholate, sodium deoxycholate, sodium dodecylsulfate and C-16 TAB. In preferred embodiment, a non-limiting example of an ionic detergent useful in an embodiment of the present invention is sodium deoxycholate.

Non-limiting examples of non-ionic detergents include, but not limited to, Brij 35, n-alkyl PEO monoether such as, polyoxyethylen(20)cetyl ether, Lubrol PX, Lubrol WX, nonidet P-40, n-alkyl phenyl PEO such as, octylphenolpoly(ethyleneglycolether)n10, and octylphenolpoly(ethyleneglycolether)n7, tetramethylbutylphenyl PEO, n-octylglucoside, octyl-thioglucopyranoside, tween-80 and tween-20, and alkylaryl polyether alcohol (Triton X-100).

Non-limiting examples of zwitterionic detergents include, but not limited to, 3-[(3-cholamidopropyl)dimthylammonio]propane-sulfonate (CHAPS), N-tetradecyl-N,N-dimethyl-3-ammoniu-1-propanesulfonate, cholic acid sulfobetaine, lauryldimethylbetaine (Empigen BB) and zwittergent 3-14.

Non-limiting examples of glycerides include, inter alia, mono-, di- or tri-glycerides. Such triglycerides include, inter alia, vegetable oils, fish oils, animal fats, hydrogenated vegetable oils, partially hydrogenated vegetable oils, synthetic triglycerides, modified triglycerides, fractionated triglycerides, and mixtures thereof.

Non-limiting examples of bile acids include ursodeoxycholic acids, cholic acid, glycolic acid, alcoholic acid, taurocholic acid, deoxycholic acid, glycodeoxycholic acid, taurodeoxycholic acid, chenodeoxycholic acid, glycochenodeoxychloic acid, and taurochenodeoxycholic acid, ursocholic acid, 7-oxolithocholic acid, lithocholic acid 3-sulfate, norcholic acid, bisnorcholic acid, hyocholic acid, and hyodeoxycholic acid.

In preferred embodiments the compositions herein comprise, consist essentially of, or consist of pharmaceutically acceptable salts and esters of the detergents. Such salts and esters are meant to be those salts and esters which are within the scope of sound medical judgment, suitable for use in contact with the tissues of humans and animals without undue toxicity, irritation, allergic response, and the like, commensurate with a reasonable benefit/risk ratio, and effective for their intended use. Preferably a composition herein comprises, consists essentially of or consists of a bile salt, or more preferably deoxycholate salt, or more preferably sodium deoxycholate.

Among detergents, bile salts are preferred as they are particularly potent solubilizers of lipid bilayer membranes. All biologic cell membranes are composed of the same bilipid structure, and are therefore subject to solubilization by detergents. Solubilization of cell membranes by a detergent involves distribution of the detergent between lipid bilayers, destabilization of the bilayer, disintegration, and subsequent formation of mixed micelles (composed of detergent and cell membrane lipid). Bile salts, and other detergents, decrease surface tension at the border of immiscible materials and allow the breakdown of large aggregates into smaller and smaller particles. In tissue, these agents dissolve cell membranes and cause cell lysis. An inflammatory response is generated, causing the body to remove the detergent solubilized material.

Bile salts have been used to improve the aqueous solubility of phosphatidylcholine (PC) and more recently, medications like amphotericin B, Taxol, and diazepam. Highly purified phosphatidylcholine can be combined with the secondary bile salt sodium deoxycholate, an anti-microbial, benzyl alcohol, and water to form a stable, mixed micelle preparation that can be rapidly sterilized and used for intravenous administration. Pharmaceutical preparations of this mixture, known as Essentiale and Lipostabil, are marketed in other countries for treatment of liver disease and hyperlipidemia, respectively.

Bile salts may be formed from a bile acid in combination with cations such as inorganic bases, ammonia, organic bases, basic amino acids or the like. Examples of the inorganic bases include alkali metal (e.g., $Li^+$, $Na^+$ and $K^+$) and alkaline earth metal (e.g., $Mg^{2+}$, $Ca^{2+}$, $Sr^{2+}$, $Ba^{2+}$). Examples of the organic base include procaine, 2-phenylethylbenzylamine, dibenzylethylenediamine, etanolamine, di etanolamine, tris(hydroxymethyl)aminomethane, polyhydroxyalkylamine, and N-methyl glucosamine. Examples of the basic amino acid include lysine, arginine, ornithine and histidine. Example of other salts includes halogen ions. Non limiting examples of the salts that can be combined with bile acids to form bile salts include, but are not limited to, ammonium chloride, ammonium sulphate, sodium chloride, sodium bromide, sodium iodide, sodium fluoride, sodium citrate, sodium sulphate, sodium carbonate, sodium bicarbonate, sodium acetate, sodium nitrate, sodium nitrite, potassium acetate, potassium carbonate, potassium dichromate, potassium chloride, potassium bromide, magnesium bromide, magnesium chloride, potassium iodide, sodium fluoride, hydroxylamine hydrochloride, sodium fluoride, sodium silicate, diammonium phosphate, sodium thiocyanate, potassium thiocyanate, lithium thiocyanate, sodium borohydride, calcium carbonate, barium carbonate, sodium dihydrogen phosphate, lithium chloride, lithium bromide, and lithium iodide. In some embodiments, the salt ion that combines with the bile acid to form a bile salt is a cation. Non limiting examples of cations include sodium ($Na^+$), potassium (10, lithium ($Li^+$), magnesium ($Mg^{2+}$), calcium ($Ca^{2+}$), barium ($Ba^{2+}$), strontium ($Sr^{2+}$), and ammonium ($NH^{4+}$).

Examples of bile salts that can be formed from a combination of a bile acid and a cation, include, but are not limited to, sodium cholate, sodium deoxycholic, sodium cholic, sodium chenodeoxycholic, sodium 7-alpha-dehydroxylate chenodeoxycholic, sodium lithocholic, sodium ursodeoxycholic, potassium deoxychote, potassium cholate, potassium chenodeoxycholate, potassium 7-alpha-dehydroxylate chenodeoxycholate, potassium lithocholate, potassium ursodeoxycholate, lithium deoxycholate, lithium cholate, lithium chenodeoxycholate, lithium 7-alpha-dehydroxylate chenodeoxycholate, lithium lithocholate, lithium ursodeoxycholate, magnesium deoxycholate, magnesium cholate, magnesium chenodeoxycholate, magnesium 7-alpha-dehydroxylate chenodeoxycholate, magnesium lithocholate, magnesium ursodeoxycholate, ammonium cholate, ammonium deoxycholate, ammonium cholate, ammonium chenodeoxycholate, ammonium 7-alpha-dehydroxylate chenodeoxycholate, ammonium lithocholate, ammonium ursodeoxycholate, dihydroxy- and trihydroxy- and taurine or glycine conjugates of any of the above. Preferably a bile salt of the invention is sodium deoxycholate. Any of the above bile salts can be used in the compositions herein.

Other examples of bile salts include steroids having 1-3 hydroxyl groups and a five carbon atom side chain terminating in a carboxyl group, which can be conjugated to glycine or taurine.

In some embodiments, a composition herein comprises, consists essentially of, or consists of one or more esters of a bile acid. Such esters include, but are not limited to, esters formed by a combination of a bile acid with a hydrogen of a COOH group optionally substituted $C_1$-$C_6$ alkyl, $C_2$-$C_6$ alkenyl, $C_3$-$C_{10}$ cycloalkyl, $C_3$-$C_{10}$ cycloalkyl($C_1$-$C_6$)alkyl, optionally substituted $C_6$-$C_{10}$ aryl, optionally substituted $C_7$-$C_{12}$ aralkyl, di($C_6$-$C_{10}$)arylmethyl, tri($C_6$-$C_{10}$)arylmethyl, or a substituted silyl.

Examples of the optionally substituted $C_{1-6}$ alkyl include e.g., methyl, ethyl, n-propyl, n-butyl, t-butyl, n-pentyl, and n-hexyl, each may be substituted with benzyloxy, $C_{1-4}$ alkylsulfonyl (e.g., methanesulfonyl), trimethylsilyl, halogen (e.g., F, Cl, and Br), acetyl, nitrobenzoyl, mesylbenzoyl, phthalimide, succinoylimide, benzenesulfonyl, phenylthio, di-$C_{1-4}$ alkylamino (e.g., dimethylamino), pyridyl, $C_{1-4}$ alkylsulfinyl (e.g., methanesulfinyl), cyano and the like. Such substituted $C_{1-6}$ alkyl include e.g., benzyloxymethyl, 2-methanesulfonylethyl, 2-trimethylsilylethyl, 2,2,2-trichloroethyl, 2-iodoethyl, acetylmethyl, p-nitrobenzoylmethyl, p-mesylbenzoylmethyl, phthalimidemethyl, succinoylimidemethyl, benzenesulfonylmethyl, phenylthiomethyl, and 1-dimethylaminoethyl. The above $C_{2-6}$ alkenyl includes e.g., vinyl, aryl, 1-propenyl, isopropenyl, 1-butenyl, 2-butenyl, 1,1-dimethylaryl, 3-methyl and 3-butenyl. The above $C_{3-10}$ cycloalkyl includes e.g., cyclopropyl, cyclobutyl, cyclopentyl, cyclohexyl, cycloheptyl, norbornyl, and adamantyl. The above $C_{3-10}$ cycloalkyl($C_{1-6}$)alkyl includes e.g., cyclopropylmethyl, cyclopentylmethyl, and cyclohexylmethyl. The above $C_{6-10}$ aryl includes e.g., phenyl, -naphthyl, 8-naphthyl, and biphenyl, each may be substituted with nitro, halogen (e.g., F, Cl, and Br) or the like, and such substituted aryl includes e.g., p-nitrophenyl and p-chlorophenyl. The above optionally substituted $C_7$_12 aralkyl includes e.g., benzyl, 1-phenylethyl, 2-phenylethyl, phenylpropyl and naphthylmethyl, each may be substituted with nitro, $C_{1-4}$ alkoxy (e.g., methoxy), $C_{1-4}$ alkyl (e.g., methyl, ethyl), hydroxy or the like. Such substituted group is exemplified by p-nitrobenzyl, p-methoxybenzyl (PMB), or 3,5-di-t-butyl-4-hydroxybenzyl. The above di($C_{6-10}$ aryl)methyl includes benzhydryl and the $C_{6-10}$ arylmethyl includes trityl, and the substituted silyl includes trimethylsilyl and tert-butyldimethylsilyl. Examples of the active ester include organic phosphate esters (e.g., diethoxy phosphate ester and diphenoxy phosphate ester), cyanomethyl ester, and the active thioester includes esters formed with aromatic heterocyclicthio compound (e.g., 2-pyridilthio ester).

Derivatives of bile acids can also be used as detergents. Such derivatives include bile acid halides, bile acid azides, bile acid anhydrides, mixed bile acid anhydride, bile acid amide, and bile acid thioester. The bile acid halide includes bile acid chloride such as deoxycholic chloride and bile acid bromide such as deoxycholic acid bromide; the mixed bile acid anhydride includes mixed monoalkylcarboxylic acid anhydride, mixed alphatic carboxylic acid anhydride, aromatic carboxylic acid anhydride, organic sulfonic acid anhydride, and wherein the active amide includes amide formed with heterocyclic compound containing N atom.

The pharmacologically active detergents (including bile acids and bile salts) are preferably micelle-forming compounds. Micelles can significantly increase the solubility of hydrophobic molecules not ordinarily soluble in water (e.g., the lipids that comprise cell membranes) by burying their hydrophobic portions away from aqueous solvent (e.g., water). In some embodiments, a composition herein comprises homogenous micelles (micelles produced by a single detergent). In some embodiments, a composition herein comprises mixed micellar formations (micelles produced by two or more compounds—one of which is a detergent).

In some embodiments, a composition comprising micelles with an average size in the range of $10^{-9}$ m-$10^{-5}$ m, $10^{-6}$, $5\times10^{-9}$ m-$10^{-6}$ m, $10\times10^{-9}$ m-$10^{-7}$, or $50\times10^{-9}$-$10\times10^{-8}$ m. In some embodiments, an average size of a micelle in a composition of the present invention may be up to $10^{-5}$, $10^{-6}$, $10^{-7}$, $10^{-8}$, $10^{-9}$ m. In some embodiments, an average size of a micelle in a composition of the present invention may be greater than $10^{-5}$, $10^{-6}$, $10^{-7}$, $10^{-8}$, $10^{-9}$ m. Moreover, the shape of the micelle can vary and can be, for example, prolate, oblate or spherical; spherical micelles are most typical.

Table 1 below illustrates several detergents contemplated by the present invention, their monomeric molecular weight of these detergents as monomers, and their critical micellar concentration (CMCs), which is the minimum concentration at which the detergent is predominantly in the form of micelles.

TABLE 1

| Detergent Name | Molecular Weight (AMU) | Micellar Molecular Weight (AMU) | CMC in H2O (M) |
| --- | --- | --- | --- |
| Anionic | | | |
| Cholate | 430 | 4300 | $1.4 \times 10-2$ |
| Deoxycholate | 415-432 | 4200 | $5 \times 10-3$ |
| Sodium dodecyl sulfate | 288 | 18000 | $8.3 \times 10-3$ |
| Cationic | | | |
| C16-TAB | 365 | 62000 | $1 \times 10-3$ |
| Amphoteric (Zwiterionic) | | | |
| Cholic acid-sulfobetaine | 615 | 6150 | $4 \times 10-3$ |
| Cholic acid-sulfobetaine | 631 | 6940 | $8 \times 10-3$ |
| Lysophophatidylcholine | 495 | 92000 | $7 \times 10-6$ |
| Zwitergent 3-14 | 364 | 30000 | $3 \times 10-4$ |
| Non-Ionic | | | |
| Brij 35 | 1225 | 49000 | $9 \times 10-5$ |
| polyoxylethylen(20)cetyl ether | 1120 | 82000 | $7.7 \times 10-5$ |
| Lubrol PX | 582 | 64000 | $1 \times 10-4$ |
| Nonidet P-40 | 603 | 90000 | $3 \times 10-4$ |
| Octylphenolpoly (ethyleneglycolether)n10 | 647 | 90000 | $0.2 \times 10-3$ |
| Octylphenolpoly (ethyleneglycolether)n7 | 515 | | $0.2 \times 10-3$ |
| n-Octylglucoside | 292 | 8000 | $14.5 \times 10-3$ |
| Octyl-thioglucopyranoside | 308 | | $9 \times 10-3$ |
| Tween-80 | 1310 | 76000 | $1.2 \times 10-5$ |
| Tween-20 | 1228 | | $6.0 \times 10-5$ |

In some embodiments, the concentration of the one or more pharmacologically active detergents (e.g., bile acids or bile salts) in a composition is such that it is at approximately the CMC concentration (i.e., +/−5 mM), or above the CMC level (e.g., more than 1, 5, 10 15, 20, 25, 30, 35, 40, 50, 55, 60, 65, 70, 75, 80, 85, 90, 99, 150, 200, 400, 800, 1600, 3200, 6800, 13,600, 27,200, or 54,400%, above the CMC concentration level).

In some embodiments, at least 10, 15, 20, 25, 30, 35, 40, 45, 50, 55, 60, 65, 70, 75, 80, 85, 90, 95, or 99% of the detergents (e.g., bile acids and bile salts), in the compositions are in micellar formation. In other embodiments, up to 90, 80, 70, 60, 50, 40, 30, 20, 10, or 5% of the detergents (e.g., bile acid(s) and/or bile salt(s)), in the compositions are in micellar formation. In other embodiments, about 10-90, 20-80, 30-70, 40-60, or about 50% of the detergents (e.g., bile acids and bile salts), of the compositions are in micellar formation.

In some embodiments, an average molecular weight of a micelle in a composition of the present invention may be up to 100,000, 50,000, 40,000, 30,000, 20,000, 10,000, 9,000, 8,000, 7,000, 6,000, 5,000, 4,000, 3,000, 2,000, 1,000, or 500 Daltons (D). In some embodiments, an average molecular weight of a micelle in a composition of the present invention may be greater than 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, or 15,000 D. In some embodiments, an average molecular weight of a micelle in a composition of the present invention may be in the range of 100-20,000, 1,000-10,000, 2,000-1,000, or 3,000-5,000 D.

In any of the embodiments herein the concentration of the one or more pharmacologically active detergents (e.g., bile acid(s) and/or bile salt(s) or more preferably sodium deoxycholate) can be up to 20, 19, 18, 17, 16, 15, 14, 13, 12, 11, 10, 9, 8, 7, 6, 5, 4, 3, 2, 1, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001% w/w, w/v or v/v. Preferably, a composition herein comprises a bile salt, such as sodium deoxycholate, wherein the concentration of the bile salt is up to 5, 4, 3, 2 or 1% w/w.

In any of the embodiments herein the concentration of the one or more pharmacologically active detergents (e.g., bile acid(s) and/or bile salt(s) or more preferably sodium deoxycholate) is greater than 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.00, 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50, 9.75, or 10.00% w/w, w/v, or v/v. Preferably, a composition herein comprises one or more bile salts, such as sodium deoxycholate at a concentration of more than 0.0001, 0.001, 0.01 or 0.1% w/w.

In any of the embodiments herein, the concentration of the pharmacologically active detergent(s) (e.g., bile acid(s) and/or bile salt(s)) is approximately in the range 0.0001-50, 0.001-40, 0.01-30, 0.02-29, 0.03-28, 0.04-27, 0.05-26, 0.06-25, 0.07-24, 0.08-23, 0.09-22, 0.1-21, 0.2-20, 0.3-19, 0.4-18, 0.5-17, 0.6-16, 0.7-15, 0.8-14, 0.9-12, or approximately in the range of 1-10% w/w, w/v or v/v. Preferably, the concentration of the one or more of the pharmacologically active detergents (e.g., bile acids or bile salts) in a composition of the invention in the range from approximately 0.005-15%, 0.01-10%, 0.05-15%, 0.10-1%, 0.1-10% or 0.5-1%, 0.5-5% w/w, w/v or v/v. It is understood that the final concentration is dependent on many factors known to persons skilled in the art including, but not limited to, location and size of the target site.

In some embodiments, a composition contains up to 10, 9.5, 9.0, 8.5, 8.0, 7.5, 7.0, 6.5, 6.0, 5.5, 5.0, 4.5, 4.0, 3.5, 3.0, 2.5, 2.0, 1.5, 1.0, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001 grams of the one or more pharmacologically active detergent(s) (e.g., bile acid(s) and/or bile salt(s)), or more preferably up to 5, 4, 3, 2, 1, 0.5, 0.4, 0.3, 0.2 or 0.1 grams of a bile salt such as sodium deoxycholate.

In some embodiments, a composition contains more than 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0 4.5, 5.0, 5.5, 6.0, 6.5, 7.0, 7.5, 8.0, 8.5, 9.0, 9.5, or 10.0 grams of the one or more pharmacologically active detergents (e.g., bile acids or bile salts), or more preferably, more than 0.01, 0.02, 0.03, 0.04, 0.05, 0.06, 0.07, 0.08 or 0.09 grams.

In some embodiments, a composition herein contains between 0.0001-10, 0.0005-5, 0.001-8, 0.005-7, 0.01-6, 0.05-5, 0.1-4, 0.5-4, or 1-3 grams of the one or more pharmacologically active detergent(s) (e.g., bile acid(s) and/or bile salt(s)), or more preferably, between 0.001-10, 0.002-9, 0.003-8, 0.004-7, 0.005-6, 0.006-5, 0.007-4, 0.008-3, 0.009-2, 0.01-1, 0.02-0.5, 0.03-0.4, 0.04-0.3, 0.05-0.2 or 0.06-0.1 grams of the one or more detergents (e.g. sodium deoxycholate).

In some embodiments herein, a composition includes one or more lipids, phospholipids, or phosphatidylcholine. Preferably, the amount of lipids, phospholipids, or phosphatidylcholine in a composition is at a concentration up to 50, 40, 30, 20, 15, 10, 9, 8, 7, 6, 5, 4, 3, 2, 1, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001% (w/w, w/v, or v/v). In preferred embodiments, the amount of lipids, phospholipids, or phosphatidylcholine in a composition is up to 5% (w/w, w/v, or v/v). For example, the present invention contemplates a composition comprising one or more detergents, preferably bile salts, or more preferably sodium deoxycholate wherein the composition includes up to 5, 4.9, 4.8, 4.7, 4.6, 4.5, 4.4, 4.3, 4.2, 4.1, 4.0, 3.0, 2.0, or 1.0% lipids or phospholipids or phosphatidylcholine.

In some embodiments, the ratio between the detergent(s) and lipids, phospholipids, or phosphatidylcholine is such that there is more detergents by mass than lipids, phospholipids or phosphatidylcholine respectively. For example, in some embodiments, the mass ratio (% w/w) of detergent(s) and lipids, phospholipids, or phosphatidylcholine is greater than 1.0, 1.2, 1.4, 1.6, 1.8, 2.0, 2.2, 2.4, 2.6, 2.8, or 3.0% w/w. For example, in some embodiments, a composition herein can include 5% w/w sodium deoxycholate and 4% w/w phosphatidylcholine. In some embodiments, the ratio of % w/v of detergent(s) and lipids, phospholipids or phosphatidylcholine is greater than 1.0, 1.2, 1.4, 1.6, 1.8, 2.0, 2.2, 2.4, 2.6, 2.8, or 3.0% w/v. Furthermore, in some embodiments, the ratio of % v/v of detergent(s) and lipids, phospholipids or phosphatidylcholine is greater than 1.0, 1.2, 1.4, 1.6, 1.8, 2.0, 2.2, 2.4, 2.6, 2.8, or 3.0% v/v.

In some embodiments, the compositions herein do not include phosphatidylcholine, phospholipids, or lipids. In some embodiments, the compositions herein do not include lipase or colipase, lipase and colipase, a platelet activating factor inhibitor, or all enzymes. In some embodiments, the compositions herein do not include testosterone, prostaglandins, progesterone, estrogen, or steroids. In some embodiments, the compositions herein do not include tyloxapol or another alkylaryl polyether alcohol. In some embodiments, the compositions herein do not include carprofen, a non-steroidal anti-inflammatory compound, or any anti-inflammatory compound. In some embodiments, the compositions herein do not include lipids, oils, fatty acids, triglycerides or polyacrylamides or a combination thereof. Any of the above or all of the above may be excluded from the composition herein.

The compositions herein can be formulated for various types of delivery e.g., topical, subcutaneous, subdermal, intra-adipocyte, intramuscular etc. by any means known in the art. Such formulations can be in the form of a tablet, powder, gel, solution, cream, vapor, ointment, etc. Preferable, the pharmacologically active detergent(s), more preferably bile acid(s) and/or bile salt(s), more preferably deoxycholic acid or salt thereof, or more preferably sodium deoxycholate, are formulated into a solution. Preferably, such solution is aqueous. The term "aqueous" as used herein refers to a solution which is a homogenous mixture prepared by dissolving a solid or a liquid in water such that the molecules of the solute or dissolved substance are dispersed among those of water. Pharmacologically acceptable aqueous vehicles for the compositions of the present invention can include, for example, any liquid solution that is capable of dissolving a detergent and is not toxic to the particular individual receiving the formulation. Examples of pharmaceutically acceptable aqueous vehicles include, without limitation, saline, water, benzyl alcohol and acetic acid. Typically, pharmaceutically acceptable aqueous vehicles are sterile.

In some embodiments, compositions herein are formulated for veterinary applications with one or more veterinary excipients. In some embodiments, compositions herein are formulated for cosmetic applications with one or more cosmetic excipients. For delivery into humans (e.g., transdermally or subcutaneously), the compositions herein are formulated with one or more pharmaceutical excipients.

Examples of pharmaceutical excipients include: buffers, diluents, lubricating agents, solubilizers, solvents; surfactants, penetration enhancers, polymers, dispersion agents, wetting agents, emulsifying and suspending agents, and preserving agents. Examples of dispersion agents include, but are not limited to, hyaluronidase and collagenase. Hyaluronidase functions to augment tissue permeability and spread or dispersion of other drugs. Collagenase has been used to isolate adipocytes from subcutaneous fat and does not have lytic effects on adipocytes themselves. Additionally hyaluronidase and collagenase can facilitate healing by accelerating reduction of necrotic tissue after treatment with the detergent formulations of the present invention. In some embodiments, the dispersion agents, such as collagenase, are administered prior to the administration of the detergent(s) herein. This may help release the adipocytes from the extracellular matrix to enhance their exposure to the detergent(s).

Examples of wetting agents include, but not limited to, acetylene glycols, acetylene alcohols, glycol ethers, alkylene glycols, lower alcohols, and nonionic surface active agents. Further, other alcohols, water-soluble organic solvents, anionic surface active agents, cationic surface active agents, amphoteric surface active agents, and saccharides may be used singly or in combination of two or more thereof. Some examples of lower alcohols include but not limited to, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol and water-soluble organic solvents such as ethylene glycol, diethylene glycol, triethylene glycol, propylene glycol, tetraethylene glycol, polyethylene glycol, dipropylene glycol, polypropylene glycol, hexylene glycol, thiodiglycol, glycerin, and 1,2,6-hexanetriol. In preferred embodiments, an excipient is an organic solvent, more preferably organic alcohols, or more preferably benzyl alcohol.

Examples of lubricating agents include, but not limited to, talc, magnesium stearate, stearic acid, and silica gel.

Examples of the preserving agents include, but not limited to, benzalkonium chloride, benzethonium chloride, chlorobutanol, phenylethyl alcohol, paraoxybenzoic acid esters, and the like. Few examples of penetration enhancers are, but not limited to, dimethylsulfoxide, n-decyl methyl sulfoxide, N,N-dimethylacetamide, N,N-methyl-2-pyrrolidone, and octylphenylpolyethylene glycols.

Examples of suitable emulsifiers include, but not limited to, sodium lauryl sulfate, sodium cetyl stearyl sulfate, sucrose stearate, and Polysorbate 80.

Examples of anionic surfactants include, but are not limited to, fatty acid soaps, N-acylamino acids, alkyl ether carboxylates, acylated peptides, alkylbenzenesulfonates, alkylnaphthalenesulfonates, naphthalenesulfonate-formalin polymerization condensates, melaminesulfonate-formalin polymerization condensates, dialkylsulfosuccinic ester salts, alkylsulfoacetates, α-olefinsulfonates, N-acylmethyltaurine, sulfated oil, higher alcohol sulfuric ester salts, secondary higher alcohol sulfuric ester salts, alkylether sulfates, secondary higher alcohol ethoxysulfates, polyoxyethylene alkylphenyl ether sulfates, monoglysulfates, fatty acid alkylolamide sulfuric ester salts, alkyl ether phosphoric ester salts, and alkylphosphoric ester salts.

Examples of nonionic surfactants include, but are not limited to, polyoxyethylene alkyl ethers, single chain length polyoxyethylene alkyl ethers, polyoxyethylene secondary alcohol ethers, polyoxyethylene alkylphenyl ethers, polyoxyethylene sterol ethers, polyoxyethylene lanoline derivatives, ethylene oxide derivatives of alkylphenol-formalin condensates, polyoxyethylene polyoxypropylene block polymers, polyoxyethylene polyoxypropylene alkyl ethers, polyoxyethylene glycerol fatty acid esters, polyoxyethylene sorbitan fatty acid esters, polyoxyethylene sorbitol fatty acid esters, polyethyleneglycol fatty acid esters, fatty acid monoglycerides, polyglycerol fatty acid esters, sorbitan fatty acid esters, propyleneglycol fatty acid esters, sucrose fatty acid esters, fatty acid alkanolamides, polyoxyethylene fatty acid amides, polyoxyethylene alkylamines, alkylamine oxides, polyoxyethylene castor oil derivatives, polyvinylpyrrolidone, polyvinyl alcohol, carboxymethyl cellulose, lecithin, gelatin, and hyaluronic acid. Any and all of the above may be used in combination with one another as appropriate.

Other examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, phosphatidylcholine, cellulose, sterile water, syrup, and methyl cellulose.

In some embodiments, a composition herein comprises: (i) a therapeutically effective amount of one or more pharmacologically active detergent(s) (e.g., bile acid(s) and/or bile salt(s)); (ii) one or more pharmaceutical, veterinary, or cosmetic excipient(s); and optionally one or more lipids, wherein the ratio of lipids and pharmacologically active detergent(s) is up to (but optionally not including) 1% w/w, w/v or v/v and wherein the solution does not include lipase or colipase. When the pharmacologically active detergent is a bile acid, in some embodiments, the bile acid is selected from the group consisting of: deoxycholic acid, cholic acid, chenodeoxycholic acid, 7-alpha-dehydroxylate chenodeoxycholic acid, lithocholic acid, ursodeoxycholic acid, dihydroxytaurin acid, trihydroxytaurine acid, and glycine conjugates of any of the above. When the pharmacologically active detergent is a bile salt, the salt preferably includes a cation selected from the group consisting of: sodium ($Na^+$), potassium ($K^+$), lithium (Li$^+$), magnesium (Mg$^{2+}$), calcium (Ca$^{2+}$), barium (Ba$^{2+}$), strontium (Sr$^{2+}$), and ammonium (NH$^{4+}$) in combination with a bile acid listed above. In some embodiment the cation is an alkali metal, such as those selected from the group consisting of alkali metal is sodium (Na$^+$), potassium (K$^+$), and lithium (Li$^+$). In some embodiments, the cation is an alkaline earth metal, such as those selected from the group consisting of: magnesium (Mg$^{2+}$), calcium (Ca$^{2+}$), barium (Ba$^{2+}$), and strontium (Sr$^{2+}$). Preferably, a solution comprises a bile acid salt wherein the bile salt is sodium deoxycholate.

The pharmacologically active detergent(s), more preferably bile acid(s) and/or bile salt(s), more preferably deoxycholic acid or salt thereof, or more preferably sodium deoxycholate is administered at various concentrations such that a therapeutically effective amount is delivered to a subject. A therapeutically effective amount is the amount of detergent(s) effective to reduce the size of a subcutaneous fat deposit or reduce the amount or appearance of loose skin. In some embodiments, a composition with a therapeutically effective amount of detergent(s) comprises between about 0.001 to 10, 0.01 to 5, or 0.01 and 2% w/w, w/v, or v/v of the detergent(s). In some embodiments, a therapeutically effective amount of the detergent(s) is less than 5, 2, 1, 0.5, 0.2, 0.1, 0.05, 0.02, or 0.01 grams of detergent(s). If one or more lipids are also included in the composition, the mass ratio of the detergent(s) and lipid(s) is preferably greater than 1 w/w, w/v, or v/v. For example, a solution of the present invention can include about 5% bile salts (e.g., sodium deoxycholate) and up to but not including 5% w/w, w/v, or v/v lipids, phospholipids, phosphatidylcholine.

When the composition is formulated as a solution (preferably aqueous solution), it may be in a container, such as a syringe or a syringe loadable container. A solution in a container or a unit dose of a solution herein is preferably up to 500, 250, 100, 25, 10, or 2.5 mL.

Aside from the detergent(s), the compositions/solutions herein can also include additional active ingredient(s) or second therapeutic agent(s). In some embodiments, such second therapeutic agents are selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents.

Additional Active Ingredients

In some embodiments of the present invention, a composition can be co-formulated, co-administered, and/or co-marketed with one or more additional active ingredients, such as, for example, anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents.

Examples of anti-microbial agents suitable for use in the compositions, methods, and kits herein include, but not limited to, anti-bactericidal agents, anti-fungal agents, anti-viral agents and the like, and are preferably efficacious against a broad spectrum of microbes.

Examples of anti-fungal agents that can be used with the composition, methods, and kits herein include dithiocarbamates, phthalimides, dicarboximides, organophosphates, benzimidazoles, carboxanilides, phenylamides, phosphites, and the like.

Examples of anti-bacterial agents include, but are not limited to, erythromycin, clarithromycin, penicillins, cephalosporins, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, penems, carbapenems, monobactams mupirocin, neomycin sulfate bacitracin, polymyxin B, 1-ofloxacin, tetracyclines (chlortetracycline hydrochloride, oxytetracycline hydrochloride and tetrachcycline hydrochloride), clindamycin phosphate, gentamicin sulfate, benzalkonium chloride, benzethonium chloride, hexylresorcinol, methylbenzethonium chloride, phenol, quaternary ammonium compounds, triclocarbon, triclosan, tea tree oil, and their pharmaceutically acceptable salts, and pharmaceutically acceptable salts and esters thereof.

Other examples of anti-bacterial agents include, but are not limited to, Acrofloxacin, Amoxicillin plus clavulonic acid (i.e., Augmentin), Amikacin, Amplicillin, Apalcillin, Apramycin, Astromicin, Arbekacin, Aspoxicillin, Azidozillin, Azithromycin, Azlocillin, Bacitracin, Benzathine penicillin, Benzylpenicillin, Carbencillin, Cefaclor, Cefadroxil, Cefalexin, Cefamandole, Cefaparin, Cefatrizine, Cefazolin, Cefbuperazone, Cefcapene, Cefdinir, Cefditoren, Cefepime, Cefetamet, Cefixime, Cefmetazole, Cefminox, Cefoperazone, Ceforanide, Cefotaxime, Cefotetan, Cefotiam, Cefoxitin, Cefpimizole, Cefpiramide, Cefpodoxime, Cefprozil, Cefradine, Cefroxadine, Cefsulodin, Ceftazidime, Ceftriaxone, Cefuroxime, Chlorampenicol, Chlortetracycline, Ciclacillin, Cinoxacin, Ciprofloxacin, Clarithromycin, Clemizole penicillin, Clindamycin, Cloxacillin, Daptomycin, Demeclocycline, Desquinolone, Dibekacin, Dicloxacillin, Dirithromycin, Doxycycline, Enoxacin, Epicillin, Erthromycin, Ethambutol, Fleroxacin, Flomoxef, Flucloxacillin, Flumequine, Flurithromycin, Fosfomycin, Fosmidomycin, Fusidic acid, Gatifloxacin, Gemifloxaxin, Gentamicin, Imipenem, Imipenem plus Cilistatin combination, Isepamicin, Isoniazid, Josamycin, Kanamycin, Kasugamycin, Kitasamycin, Latamoxef, Levofloxacin, Lincomycin, Linezolid, Lomefloxacin, Loracarbaf, Lymecycline, Mecillinam, Meropenem, Methacycline, Methicillin, Metronidazole, Mezlocillin, Midecamycin, Minocycline, Miokamycin, Moxifloxacin, Nafcillin, Nafcillin, Nalidixic acid, Neomycin, Netilmicin, Norfloxacin, Novobiocin, Oflaxacin, Oleandomycin, Oxacillin, Oxolinic acid, Oxytetracycline, Paromycin, Pazufloxacin, Pefloxacin, Penicillin G, Penicillin V, Phenethicillin, Phenoxymethyl penicillin, Pipemidic acid, Piperacillin, Piperacillin and Tazobactam combination, Piromidic acid, Procaine penicillin, Propicillin, Pyrimethamine, Rifabutin, Rifamide, Rifampicin, Rifamycin SV, Rifapentene, Rokitamycin, Rolitetracycline, Roxithromycin, Rufloxacin, Sitafloxacin, Sparfloxacin, Spectinomycin, Spiramycin, Sulfadiazine, Sulfadoxine, Sulfamethoxazole, Sisomicin, Streptomycin, Sulfamethoxazole, Sulfisoxazole, Synercid (Quinupristan-Dalfopristan combination), Teicoplanin, Telithromycin, Temocillin, Tetracycline, Tetroxoprim, Thiamphenicol, Ticarcillin, Tigecycline, Tobramycin, Tosufloxacin, Trimethoprim, Trimetrexate, Trovafloxacin, Vancomycin, and Verdamicin.

Examples of vasoconstrictor agents that can be used with the compositions, methods, and kits of the present invention include dihydroergotamine, ergotamine and methysergide, and pharmaceutically-acceptable salts thereof.

Examples of anti-thrombotic agents that can be used with the compositions, methods, and kits of the present invention include argatroban, iloprost, lamifiban, taprostene, tirofiban, tissue plasminogen activator (natural or recombinant), tenecteplase (TNK), and lanoteplase (nPA), factor VIIa inhibitors, factor Xa inhibitors, thrombin inhibitors (such as hirudin and argatroban), PAI-1 inhibitors (i.e., inactivators of tissue plasminogen activator inhibitors), alpha2-antiplasmin inhibitors, streptokinase, urokinase and prourokinase, and anisoylated plasminogen streptokinase activator complex, anti-coagulants (e.g., hirudin, heparin, etc.), plasminogen activators (e.g., t-PA, urokinase, etc.), fibrinolytic enzymes (e.g., plasmin, subtilisin, etc.), anti-platelet-aggregation agents (e.g., prostacyclin, aspirin, etc.) and the like.

Examples of anti-coagulation agents that can be used with the compositions, methods, and kits of the present invention include cilostazol, clopidogrel, ticlopidine, tirofiban, eptifibatide, abciximab, anagrelide, dipyridamole, aspirin, dipyridamole/aspirin, dalteparin, enoxaparin, tinzaparin, heparin (various), danaparoid, antithrombin III, lepirudin, argatroban, bivalirudin, warfarin, anisidione, alteplase, reteplase, tenecteplase, drotrecogin, anistreplase, streptokinase, urokinase, and combinations thereof.

Examples of suds-depressants that can be used with the compositions, methods and kits of the present invention include monocarboxylic fatty acid and soluble salts thereof. The monocarboxylic fatty acids and their salts can have hydrocarbyl chains of about 1 to about 50 carbon atoms, about 10 to about 24 carbon atoms, or about 12 to about 18 carbon atoms. Suitable salts include the alkali metal salts such as sodium, potassium, and lithium salts, and ammonium and alkanolammonium salts. Additional suds-depressants include, for example, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), etc. Other suds-depressants include N-alkylated amino triazines such as tri- to hexa-alkylmelamines or di- to tetra-alkyldiamine chlortriazines formed as products of cyanuric chloride with 1-5 or 2-3 moles of a primary or secondary amine containing 1 to 24 carbon atoms, propylene oxide, and monostearyl phosphates such as monostearyl alcohol phosphate ester and monostearyl di-alkali metal (e.g., $K^+$, $Na^+$, and $Li^+$) phosphates and phosphate esters. The hydrocarbons such as paraffin (including mixtures of true paraffins and cyclic hydrocarbons) and haloparaffin can be utilized in liquid form. It is also known to utilize waxy hydrocarbons, preferably having a melting point below about 100° C. The hydrocarbons constitute a preferred category of suds-suppressor for detergent compositions. The hydrocarbons can include aliphatic, alicyclic, aromatic, and heterocyclic saturated or unsaturated hydrocarbons having from about 12 to about 70 carbon atoms. Another example of suds suppressors comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed or fused onto the silica. Examples also include, but not limited to, silicones, and silica-silicone mixtures. Silicones can be generally represented by alkylated polysiloxane materials while silica is normally used in finely divided forms exemplified by silica aerogels and xerogels and hydrophobic silicas of various types. Silicone suds controlling agent, DC-544, is commercially available from Dow Corning, which is a siloxane-glycol copolymer. Other suds suppressors include mixtures of silicone oils and 2-alkyl-alcanols. Suitable 2-alkyl-alkanols are 2-butyl-octanol which are commercially available.

Examples of anti-dispersion agents that can be used with the compositions, methods, and kits herein include, but are not limited to, sucrose, glyercerol, and glycerin.

Examples of steroids that can be used with the compositions, methods, and kits herein include, but are not limited to, betamethasone, chloroprednisone, clocortolone, cortisone, desonide, dexamethasone, desoximetasone, difluprednate, estradiol, fludrocortisone, flumethasone, flunisolide, fluocortolone, fluprednisolone, hydrocortisone, meprednisone, methylprednisolone, paramethasone, prednisolone, prednisone, pregnan-3-alpha-ol-20-one, testosterone, and triamcinolone, estradiol, estron, estriol, polyestradiol, polyestriol, dienestrol, diethylstilbestrol, dihydroergosterone, cyproterone, danazol, testosterone, progesterone, norethindrone, levonorgestrol, ethynodiol, norgestimate, gestanin, 3-ketondesogestrel, demegestone, promethoestrol, testosterone, spironolactone, and esters thereof, budesonide, rofleponide, rofleponide palmitate, ciclesonide, momethasone furoate, fluticasone propionate, tipredane, fluocinolone acetonide, flunisolide, flumethasone, dexamethasone, beclomethasone dipropionate, deflazacort, cortivazol, or cortisol and/or hydrocortisol, prednisone, fluorometholone acetate, dexamethasone sodium phosphate, suprofen, fluorometholone, and medrysone, optionally in their pure isomeric forms (where such forms exist) and pharmaceutically acceptable salts thereof.

Examples of anti-inflammatory agents that can be used with the compositions, methods, and kits herein include both steroidal and non-steroidal anti-inflammatory agents. Suitable steroidal anti-inflammatory agent include, but are not limited to, corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpriorate, hydrocortamate, meprednisone, paramethasone, prednisolone, prednisone, beclomethasone dipropionate, betamethasone dipropionate, triamcinolone, and mixtures thereof.

Suitable non-steroidal anti-inflammatory agents include, but are not limited to, oxicams, such as piroxicam, isoxicam, tonexicam, sudoxicam, and CP-14,304; salicylates, such as salicylic acid, aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acemetacin, fentiazac, zomepirac, clidanac, oxepinac, and felbinac; the fenamates, such as mefenamic, meclofenamic, flufenamic, niflumic, and tolfenamic acids; propionic acid derivates, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and pyrazoles, such as phenybutazone, oxyphenbutazone, feprazone, azapropazone, and trimethazone. Mixtures of these nonsteroidal anti-inflammatory agents can also be employed, as well as the pharmaceutically-acceptable salts and esters thereof.

Examples of analgesics that can be used with the compositions, methods, and kits of the present invention to reduce discomfort due to inflammation include, but are not limited to, lidocaine, mepivacaine, bupivacaine, procaine, chloroprocaine, etidocaine, prilocalne dyclonine, hexylcaine, procaine, cocaine, ketamine, morphine, pramoxine, propophol, phenol, naloxone, meperidine, butorphanol or pentazocine, or morphine-6-glucuronide, codeine, dihydrocodeine, diamorphine, dextropropoxyphene, pethidine, fentanyl, alfentanil, alphaprodine, buprenorphine, dextromoramide, diphenoxylate, dipipanone, heroin (diacetylmorphine), hydrocodone (dihydrocodeinone), hydromorphone (dihydromorphinone), levorphanol, meptazinol, methadone, metopon (methyldihydromorphinone), nalbuphine, oxycodone (dihydrohydroxycodeinone), oxymorphone (dihydrohydroxymorphinone), phenadoxone, phenazocine, remifentanil, tramadol, tetracaine, and mixtures thereof, as well as pharmaceutically acceptable salts and esters thereof. In preferred embodiments, a composition includes an analgesic selected from the group consisting of lidocaine, hydromorphone, oxycodone, morphine and pharmaceutically-acceptable salts thereof.

Examples of tranquilizer and sedative drugs that may be included in the compositions, methods, and kits herein include, but are not limited to, chlordiazepoxide, benactyzine, benzquinamide, flurazepam, hydroxyzine, loxapine, promazine, and acceptable salts and esters thereof.

Examples of muscle relaxants that can be included in the compositions, methods, and kits herein include, but are not limited to, cinnamedrine, cyclobenzaprine, flavoxate, orphenadrine, papaverine, mebeverine, idaverine, ritodrine, dephenoxylate, dantrolene, azumolene, and pharmaceutically-acceptable salts thereof.

Examples of anti-diarrhea agents that can be included in the compositions, methods and kits herein include, but are not limited to, loperamide and pharmaceutically-acceptable salts thereof.

The examples herein and other active agents can be co-formulated or co-administered with the one or more pharmacologically active detergents (e.g bile acids or bile salts). When co-formulated with a detergent (e.g., bile salt) the additional agent can be up to 20, 19, 18, 17, 16, 15, 14, 13, 12, 11, 10, 9, 8, 7, 6, 5, 4, 3, 2, 1, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001% w/w, w/v or v/v or at greater than 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 1.0, 1.25, 1.50, 1.75, 2.0, 2.25, 2.50, 2.75, 3.0, 3.25, 3.50, 3.75, 4.0, 4.25, 4.50, 4.75, 5.0, 5.25, 5.50, 5.75, 6.0, 6.25, 6.50, 6.75, 7.0, 7.25, 7.50, 7.75, 8.0, 8.25, 8.50, 8.75, 9.0, 9.25, 9.50, 9.75, 10, 10.25, 10.50, 10.75, 11, 11.25, 11.50, 11.75, 12, 12.25, 12.50, 12.75, 13, 13.25, 13.50, 13.75, 14, 14.25, 14.50, 14.75, 15, 15.25, 15.50, 15.75, 16, 16.25, 16.50, 16.75, 17, 17.25, 17.50, 17.75, 18, 18.25, 18.50, 18.75, 19, 19.25, 19.50, 19.75, or 20% (w/w, w/v or v/v) of the composition.

In some embodiments, the additional active ingredient(s) are co-formulated with the one or more pharmacologically active detergents (e.g., bile acids or bile salts) such that they are at a concentration in the range of from approximately 0.001-50, 0.001-40, 0.01-30, 0.02-29, 0.03-28, 0.04-27, 0.05-26, 0.06-25, 0.07-24, 0.08-23, 0.09-22, 0.1-21, 0.2-20, 0.3-19, 0.4-18, 0.5-17, 0.6-16, 0.7-15, 0.8-14, 0.9-12, or 1-10% w/w, w/v or v/v of the composition.

In some embodiments, a composition contains up to 10, 9.5, 9.0, 8.5, 8.0, 7.5, 7.0, 6.5, 6.0, 5.5, 5.0, 4.5, 4.0, 3.5, 3.0, 2.5, 2.0, 1.5, 1.0, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001 grams of non-detergent active ingredient(s) or more than 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10 grams of the additional active ingredient(s) or at a range between about 0.0001-10, 0.0005-9, 0.001-8, 0.005-7, 0.01-6, 0.05-5, 0.1-4, 0.5-4, or 1-3 grams of non-detergent active ingredient(s).

In some embodiments, the pharmacologically active detergent(s) (e.g., bile acids and bile salts) herein formulated for subcutaneous or subdermal injection directly into fat deposits or under loose skin. Formulations for injection can be presented in unit dosage form, for example, in ampoules, syringe loadable containers, or in multi-dose containers, with an added preservative. The injectable formulations can take such forms as suspensions, solutions, or emulsions in oily or aqueous vehicles, and can contain agents such as suspending, stabilizing anti-dispersion and/or dispersion agents. Such formulations can further comprise active agents such as a vasodilator to prevent the compositions herein (e.g., deoxycholic acid or salt thereof) from entering into the vascular system.

The compositions of the present invention can be formulated so as to provide quick, sustained or delayed release of the active ingredient after administration to the patient by employing procedures known in the art. In some embodiments, a composition herein is formulated for slow release. A slow release formulation or a biodegradable controlled release dosage forms provide a composition for prolonging an effect of a fat-solubilizing effective amount of a bile acids or bile salts in vivo at a desired site of treatment. In some embodiments, the detergents herein (e.g. bile acids or salts thereof) are formulated with a pharmaceutically acceptable augmenting agent which is effective to further prolong the duration of effect of the detergent(s). The controlled release formulation can be formed into slabs, rods, pellets, microparticles, (e.g., microspheres, microcapsules), spheroids, pastes solution, spray, patch, etc. Such formulations can be used to form a suspension in isotonic saline or other physiological buffer or a solution acceptable for subdermal injection, for a patch, for a pump, or for a depot.

The slow release formulation can be administered by applying, implanting, inserting or injecting a composition herein (e.g., injectable microspheres loaded with a bile acid or bile salt in sustained release form) into a site at or adjacent to a target site to provide treatment. In some embodiments, the composition herein is administered to a target site using in situ gel implantation. In some embodiments, the pharmacologically active detergent(s) are entrapped in a polymer carrier such as, but not limited to, poly(DL-lactide-co-glycolide); poly(lactide-co-glycolide); poly(DL-lactide); poly(L-lactide); poly(glycolide); poly(ε-caprolactone); poly(DL-lactide-co-caprolactone).

Unit Dose

The present invention also contemplates unit doses of the compositions herein. Such unit doses are preferably in a container, a syringe or a syringe loadable container. Such unit doses can have, for example, a total volume of up to 500, 400, 300, 200, 100, 90, 80, 70, 60, 50, 40, 30, 20, 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001 mL. In some embodiments, a unit dose has a total volume in the range of 0.0001-500, 0.0005-400, 0.001-300, 0.005-200, 0.01-100, 0.05-90, 0.06-80, 0.07-70, 0.08-60, 0.09-50, 0.1-40, 0.2-30, 0.3-29, 0.4-28, 0.5-27, 0.6-26, 0.7-25, 0.8-24, 0.9-23, 10-22, 11-21, 12-20, 13-19, 14-18, or 15-17 mL per target site. Other embodiments contemplate a unit dose with a total volume in the range of 0.01-30, 0.02-20, 0.03-10, 0.4-5 or 0.5-1 mL total volume. In some embodiments, a unit dose has a total volume greater 0.0001, 0.0002, 0.0005, 0.001, 0.002, 0.005, 0.01, 0.02, 0.05, 0.1, 0.2, 0.5, 1, 2, 5, 10, 20, 50, 100 mL. Preferably, a unit dose has a total volume of up to 1.0, 0.8, 0.6, 0.4, or 0.2.

A unit dose comprises, consists essentially, or consists of an amount of the one or more pharmacologically active detergents (e.g., bile acid and bile salts, or more preferably deoxycholic acid or salts thereof) in a therapeutically effective amount. Such amount that can be determined by a person of ordinary skill in the art and will depend, in part, on the localization of the fat deposit or loose skin, size of the fat deposit or loose skin and concentration of active agent(s).

In some embodiments, a unit dose includes up to 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001 grams of the pharmacologically active detergents. In some embodiments, a unit dose includes a range of approximately 0.00001 to 10, 0.00005 to 1.0, 0.0001 to 0.5, 0.0005 to 0.1, 0.001 to 0.05, or 0.005 to 0.01 grams. Preferably a unit dose comprises about 0.01 grams of a bile acid or bile salt (e.g., sodium deoxycholate).

A unit dose can further include lipids such as phospholipids or more preferably phosphatidylcholine. Such lipids can be added in amount and concentrations identified herein. However, in preferred embodiments, a unit dose has up to 5% w/w, w/v or v/v lipids, phospholipids, or phosphatidylcholine. Preferably, the ratio of % w/w of detergent(s) and % w/w of lipids (e.g., phosphatidylcholine in a unit dose is greater than 1, greater than 1.2, 1.4, 1.6, 1.8, 2.0, 2.2, 2.4, 2.6, 2.8, or 3.0.

Uses

The compositions herein can be used to prevent or reduce the appearance of a skin condition, prevent or reduce the symptoms of sleep apnea, and prevent or reduce the appearance or effects of an adipose condition in a subject. Such subject can be an animal, more preferably a mammal, more preferably a primate (e.g., a monkey, chimpanzee, etc.), a domesticated animal (e.g., a dog, cat, horse, etc.), a farm animal (e.g., goat, sheep, pig, cattle, etc.), a laboratory animal (e.g., mouse, rat, etc.), or more preferably a human.

In some embodiments, the compositions herein are used to prevent or reduce the appearance of a skin condition selected from the group consisting of loose skin, skin aging, irregularities of the skin, and wrinkles. Such methods involve administering locally to a to a skin region of interest a composition of the invention comprising: (i) one or more pharmacologically active detergent(s), more preferably one or more bile acids or bile salts, more preferably deoxycholic acid or salt thereof, or more preferably sodium deoxycholate; (ii) a pharmaceutical, cosmetic, or veterinary excipient, and (iii) optionally one or more lipids. The one or more detergents are administered in a skin-tightening effective amount. In some embodiments, up to 5, 4, 3, 2, 1, 0.5, 0.4, 0.3, 0.2, 0.1, 0.05, 0.04, 0.03, 0.02, or 0.01 grams of detergent(s) are administered. In some embodiments, a composition includes up to 5, 4, 3, 2, 1, 0.5, 0.4, 0.3, 0.2, 0.1, 0.05, 0.04, 0.03, 0.02, or 0.01% w/w, w/v or v/v of detergent(s). When one or more lipids are optionally included, such lipids can be phospholipids or more preferably phosphatidylcholine. The mass or volume ratio (e.g., % w/w, w/v or v/v) of detergent(s) to lipid(s) in the composition delivered is preferably greater than 1. In some embodiments, a composition comprises up to 5, 4, 3, 2, 1, 0.5, 0.4, 0.3, 0.2, 0.1, 0.05, 0.04, 0.03, 0.02, or 0.01% w/w, w/v or v/v lipids, phospholipids or phosphatidylcholine. In any of the above embodiments, the compositions being administered are preferably in an aqueous solution. Such solution preferably has a total volume up to 500 mL, 100 mL, 50 mL, 10 mL or 5 mL.

The above compositions are preferably administered locally to a target area to create an inflammatory response causing a scar formation. The formation of a scar results in skin tightening especially in areas where the skin is under little or no tension and provides little resistance to scar contraction. Such treatment may be relevant in a number of clinical scenarios such as, for example, commonly performed fat treatments, including, but not limited to, large volume liposuction. The latter may be associated with post-treatment skin laxity (loose skin in areas of fat removal) and skin surface irregularities. Thus, in some embodiments a composition comprising a therapeutically effective amount of detergent(s) or bile salt(s) may be administered to a liposuction site after completion of the liposuction procedure.

In some embodiments, the target area is an area under eye, under chin, under arm, buttock, calf, back, thigh, stomach, cheek, brow, or any other skin regions showing aging, wrinkles, loose skin or skin irregularity.

In some embodiment, the compositions herein are delivered to the target area via a subdermal injection, a pump, a patch, or a subdermal depot. In some embodiments, the compositions herein are administered topically.

In one aspect, the compositions herein are used for reducing a subcutaneous fat deposit in a subject. The subcutaneous fat deposit can be associated with an adipose conditions such as, for example, obesity, fat redistribution syndrome, eyelid fat herniation, lipomas, lipodystrophy (including buffalo hump lipodystrophy), dorsocervical fat, visceral adiposity, breast enlargement, hyperadiposity, diffused body fat around trunk and arms, fat deposits associated with cellulite, Dercum's disease, Madelung's neck, lipedema, piezogenic nodules, launois cleret syndrome and xanthelasma. The subcutaneous fat deposit can be located in an area of the body, including, but not limited to, under eye, under chin, under arm, buttock, calf, back, thigh, stomach, cheek, brow, "love-handles", ankles, fingers, lips, trachea, etc.

The subcutaneous fat deposits can be reduced by administering locally to the fat deposits a composition comprising: (i) one or more pharmacologically active detergents, more preferably one or more bile acids or salts thereof, more preferably deoxycholic acid or salts thereof, or more preferably sodium deoxycholate; (ii) a pharmaceutical or veterinary excipient; and (iii) optionally a lipid, wherein the ratio of the lipid and bile acid or bile salt is up to 1% w/w. Preferably, the composition does not include lipase or colipase. The above method preferably does not include performing surgery (e.g., liposuction) on the subject.

Preferably, the one or more pharmacologically active detergents are administered in a fat-dissolving effective amount such as up to 5, 4, 3, 2, 1, 0.5, 0.4, 0.3, 0.2, 0.1, 0.05, 0.04, 0.03, 0.02, or 0.01 grams of detergent(s). In some embodiments, a composition includes up to 5, 4, 3, 2, 1, 0.5, 0.4, 0.3, 0.2, 0.1, 0.05, 0.04, 0.03, 0.02, or 0.01% w/w, w/v or v/v of detergent(s). Preferably a composition comprises between about 0.001 to 10% w/w of detergent(s) or bile salt(s), or more preferably between about 0.01 and 5% w/w detergent(s) or bile salt(s).

When one or more lipids are optionally included, such lipids can be phospholipids or more preferably phosphatidylcholine. The mass or volume ratio (e.g., % w/w, w/v or v/v) of detergent(s) to lipid(s) in the composition delivered is preferably greater than 1. In some embodiments, a composition comprises up to 5, 4, 3, 2, 1, 0.5, 0.4, 0.3, 0.2, 0.1, 0.05, 0.04, 0.03, 0.02, or 0.01% w/w, w/v or v/v lipids, phospholipids or phosphatidylcholine. In any of the above embodiments, the composition being administered is preferably in a solution or more preferably an aqueous solution. Such solution preferably has a total volume up to 500 mL, 100 mL, 50 mL, 10 mL or 5 mL.

The subcutaneous fat deposit can be associated with an adipose condition selected from the group consisting of obesity, fat redistribution syndrome, eyelid fat herniation, lipomas, Dercum's disease, lipodystrophy, buffalo hump lipodystrophy, dorsocervical fat, visceral adiposity, breast enlargement, hyperadiposity, diffused body fat around trunk and arms, and fat deposits associated with cellulite. Thus, the compositions herein can be used to treat or ameliorate conditions associated with such conditions. In some embodiments, the composition herein are administered locally under eye, under chin, under arm, buttock, calf, back, thigh, or stomach of said subject to reduce a subcutaneous fat deposit in such site.

For example, in some embodiments, a composition herein (e.g., a pharmaceutically active detergent, or more preferably a bile salt, or more preferably sodium deoxycholate) is use to treat or ameliorate lipodystrophy conditions in a subject, such as a human HIV patient. Lipodystrophy is a condition that is often a side effect from HIV treatments (e.g., treatment with protease inhibitors). Lipodystrophy is characterized by regional or generalized loss of subcutaneous fat or abnormal fat redistribution and metabolic disturbances. Signs of lipodystrophy can include a swollen belly along with loss of tissue from the face, arms and legs, which can give an appearance of sunken eyes and sticking-out cheekbones. Other signs of lipodystrophy include fat accumulates on the back of the neck, which is sometimes referred to as buffalo humps (diffused fat accumulation). Female HIV patients may also be treated for breast enlargement which is attributed to the lipodystrophy syndrome.

In some embodiments, the compositions herein are used to treat lipomas. Lipomas are localized fat accumulations that are benign neoplastic growth. There are various forms of lipomas and, in some embodiments; the compositions herein are used to treat multiple familial lipomatosis.

In some embodiments, the compositions herein are used to prevent, treat or ameliorate an adipose in an animal such as a cat, a dog or a horse.

In some embodiments, the compositions herein are used to treat obstructive sleep apnea. Obstructive sleep apnea is characterized by repetitive pauses in breathing during sleep due to the obstruction and/or collapse of an upper airway (throat), usually accompanied by a reduction in blood oxygen saturation, and followed by an awakening to breathe. It is a dangerous (sometimes life threatening) condition that often affects obese people. Obese people have a large amount of fat around their trachea, and this fat may cause their airway to collapse when their muscles relax during sleep. In one embodiment, the compositions herein (e.g., sodium deoxycholate) are used to treat obstructive sleep apnea by dissolving fat around the trachea. In such embodiments, a composition of the invention is administered locally (e.g., via injection) to a target site of fat around the trachea in a therapeutically effective amount.

For the treatment of an adipose condition, the compositions herein (e.g., pharmacologically active detergent(s), bile salt(s), or sodium deoxycholate) are preferably administered locally to the site of fat accumulation. Localized delivery can be made via, e.g., subcutaneous or transdermal injection, external or internal pump, dermal patch, subcutaneous depot, or any other means known in the art.

In some embodiments, a composition herein is delivered via a dermal patch. A dermal patch is a self-adhesive unit, and is worn on a patient's body. It delivers small doses of a drug into the skin, where it then diffuses into the skin. The patch incorporates a series of thin, flexible films: a backing layer, a drug reservoir, a rate-controlling film and an adhesive. Enhancers may be added to further increase drug permeation through the skin. The patch can be coupled with a low-level electrical energy to actively transport drugs through intact skin.

In some embodiments, a composition herein is delivered via an external or internal pump. A pump is a specialized device, which delivers drug into the body via a small catheter. For example, an infusion pump can be programmed to deliver drugs at precise dosages and delivery rates. These pumps may have a feedback device that controls drug delivery according to need. A size of the pump depends on an amount of a drug and intended length of treatment.

In some embodiments, a composition herein is delivered via a depot. A depot is a non-biodegradable and an osmotically driven implant which is used to enable delivery of drugs for therapy. Powered by osmosis, the depot incorporates a miniature metal alloy cylinder and can provide continuous drug delivery from days to up to one year. In some embodiments, the compositions herein may be administered parenterally. Parenteral routes of administration involve injections into various compartments of the body such as but not limited to, intravenous, subcutaneous, intramuscular, intraperitoneal and the like.

In one example, two injections of up to 1 mL each are administered under the chin wherein each injection comprises between 0.005 and 0.5, or more preferably between 0.002 and 0.08 grams sodium deoxycholate. In another embodiment 3 treatments of 2 mL 1% w/w sodium deoxycholate are administered to a cheek area.

In any of the embodiments herein, a therapeutic regimen can include administering one or more unit doses to a target site. A target site can be for example 0.1 $cm^2$, to about 5 $cm^2$. The compositions herein may be administered at the same, adjacent, or nearby target sites at various intervals, dosages, volumes, as disclosed herein. When delivered, the compositions can be administered at various levels below the dermis, including, for example, 0.1-4, 0.2-3.5, 0.3-3, 0.4-2.5, or 0.5-2 inches below the dermis.

For example, in some embodiments up to 100, 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02 or 0.01 mL of a solution is delivered locally to a target site (e.g., a site of fat accumulation or loose skin) at a time. The solution can comprise, consist essentially of, or consist of one or more pharmacologically active detergent(s), (e.g. bile acids or salts thereof, or more preferably deoxycholic acid or salts thereof, more preferably sodium deoxycholate) wherein the solution contains up to 5, 4, 3, 2, 1% w/w of the detergent(s). Such a solution can include up to 5% w/w, w/v, or v/v lipids, or phospholipids, or phosphatidylcholine, or in some embodiments no phosphatidylcholine. In some embodiments, the compositions (e.g., solutions) herein include no lipase or no colipase, or no colipase and lipase. In some embodiments, the compositions (e.g., solutions) herein include no enzymes. In some embodiments up to 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02 or 0.01 grams of the detergent(s) herein (preferably bile acids or bile salts) are administered locally to a target site at a time. In other embodiments more than 0.001, 0.002, 0.003, 0.004, 0.005, 0.006, 0.007, 0.008, 0.009 or 0.01 g is delivered to a target site at a time. Generally, the total volume, unit dose and number of treatments administered will vary depending on the amount of fat in a target site, the location of the target site, type of fat composition, and desired results. In general, the greater is the amount of fat being treated, the greater is the dose that is administered. Also, the greater the amount of loose skin in a target area, the greater the dose or the more number of injections that will be delivered. It should be noted that while the compositions and unit dosages herein may be administered into an individual as part of a treatment regimen, they are not necessarily actively removed from the individual as part of the treatment regimen (e.g., via suction).

In any of the embodiments herein, a therapeutic regimen can include administration to a target site at least 1, 2, 3, 4, 5, 6, 7, 8, 9, or 10 unit doses. Such unit doses can be delivered simultaneously or over a period of time. For example administration can occur once, twice, three or four times an hour, a day, a week, a month, or a year. In some embodiments, multiple administrations involve between 1-100, 2-50, 3-30, 4-20, or 5-10 administrations to a target site an hour, a day, a week, a month or a year. In some embodiments, multiple administrations involve up to 10, 9, 8, 7, 6, 5, 4, 3, or 2 administrations to a target site a year, a week, a day or an hour. The total number of administrations in a therapeutic regimen can be completed with a period of 1 year, 6 months, 5 months, 4 months, 3 months, 2 months, 1 month, 3 weeks, 2, weeks, or 1 week or less.

In any of the embodiments herein, the methods do not include the surgical removal of one or more localized fat deposits in a subject. A non-surgical method of fat reduction does not include liposuction, lipoplasty or suction lipectomy. For example, in some embodiments, the non-surgical methods herein do not include liposuction. In some embodiments, the methods herein also exclude non-invasive means for reducing fat, e.g., ultrasonification. In other embodiments, non-invasive means can be used in conjunction with the compositions herein.

Any of the treatments disclosed may be supplemented by further administering to the patient additional active agent(s). Such additional agent(s) can be administered separately or in combination with the compositions herein. A second agent can be administered locally or systemically. In some embodiments, a second agent is co-formulated with the detergent(s). In other embodiments, second agents are administered prior to, simultaneous with, or after the administration of the detergents.

Kits

Figure 11:
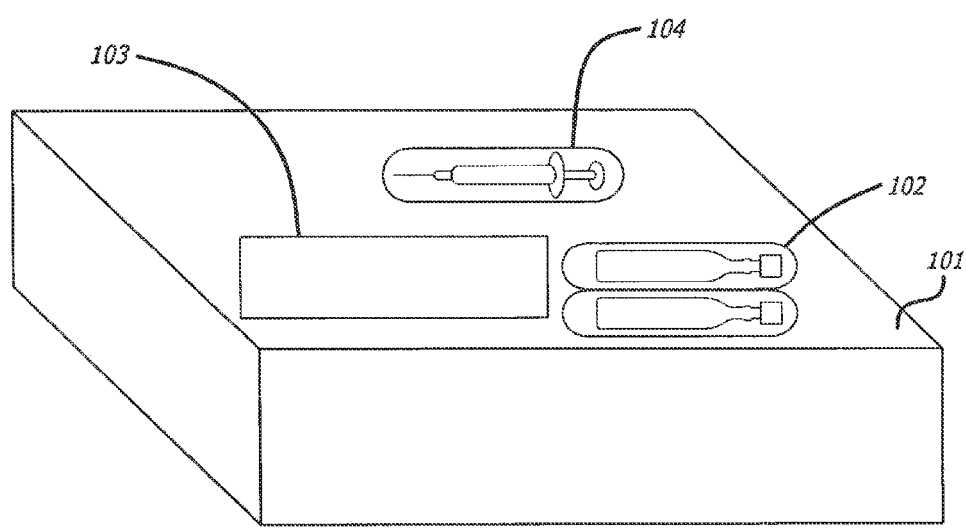
FIG. 11 depicts a kit for reducing a subcutaneous fat accumulation.

FIG. 11 is an illustration of a kit 101 for non-surgical reduction of subcutaneous fat and/or tightening of loose skin. Kit 101 includes one or more containers 102. For example, a first container 102 can include a therapeutically effective amount of a pharmacologically active detergent (e.g., bile acids and salts thereof) and up to 5% w/v phosphatidylcholine and a second container 102 can include a therapeutically effective amount of a pharmacologically active detergent and no phosphatidylcholine. Containers 102 are preferably syringe loadable. Containers 102 can each hold one or more unit doses. For example, a container 102 can hold up to 500, 100, 20, 10, 5 or 1 mL.

In some embodiments, a container 102 can include one or more additional active ingredients, either independently of or in combination with the one or more detergents herein. Examples of additional active ingredients include antimicrobial agents, anti-thrombotic agents, anti-coagulation agents, suds-depressants, anti-inflammatory agents, analgesics, anesthetics, anti-dispersion agents, dispersion agents, penetration enhancers, steroids, tranquilizers, muscle relaxants, and anti-diarrhea agents.

In one example, a container 102 includes up to 5% w/v of phospholipids (e.g. phosphatidylcholine) or no phospholipids (e.g. phosphatidylcholine) and up to 10, 5.0, 1.0, or 0.5% w/w detergent(s).

In one example, a container 102 contains more than 0.01, 0.1, 1.0, 2.0, 3.0, 4.0, or 5.0% w/w, w/v or v/v pharmacologically active detergent(s) (e.g., bile acids or bile salts) and up to 5% w/v phospholipids (e.g. phosphatidylcholine) or no phospholipids (e.g. phosphatidylcholine).

The solution of container 102 is administered according to the instructions for use 103. Instructions for use 103 can provide dosing instructions which may depend upon, for example, location of target site, animal being treated, desired results, size of target site, concentration of detergent(s) in composition, etc. Preferably instructions for use 103 are for the treatment of an animal such as a human, a dog, a cat, or a horse. Instructions for use 103 can also include information for treatment of other domesticated animals and/or farm animals. Instruction for use 103 may also include information on the use of the compositions herein to treat specific target sites, such as, e.g., fat deposits or areas of loose skin localized under eye, under chin, under arm, buttock, cheek, brow, calf, back, thigh, ankle, or stomach. In some embodiments, instruction for use 103 detail an explanation for use of the compositions herein to treat a fat condition of obesity, fat redistribution syndrome, dorsocervical fat, visceral adiposity, breast enlargement, hyperadiposity, eyelid fat herniation, lipomas, lipodystrophy, buffalo hump lipodystrophy, diffused body fat around trunk and arms, or fat deposits associated with cellulite.

In some embodiments, instructions for use 103 detail an explanation for use of the compositions herein to treat a skin condition selected from the group consisting of loose skin, skin aging, irregularities of the skin, and wrinkles.

Instruction for use 103 may include information regarding proper diluents and volumes for dilution, if any, of the container 102. The instructions for use 103 may also provide information regarding the proper administration of the compositions herein, such as frequency and dosage of administration.

Kit 101 can comprise alternatively or in addition to container 102 one or more syringes 104 or other suitable delivery devices (e.g., patches, subcutaneous depots) for delivering the compositions herein (e.g. those in container 102) to a target site of fat accumulation or loose skin. In some embodiments, syringe or other delivery device 104 may be preloaded with one or more unit doses of the compositions herein.

Preferably, a kit includes one or more syringes for local subcutaneous injection of a solution having total volume up to 100 mL containing between 0.1-10% of a bile acid or a salt, or more preferably deoxycholic acid or salt thereof or sodium deoxycholate. The solution preferably does not contain lipase or colipase or both. The solution preferably contains up to or no phosphatidylcholine.

The invention contemplates kits having a first container comprising a pharmacologically active detergent and up to 5% w/v phosphatidylcholine, as well as written instructions for reducing subcutaneous fat deposits in a mammal without the use of surgery. Preferably, the kits herein may be used to reduce fat deposits in a variety of mammals such as, for example, a human, a horse, a dog, or a cat. In some embodiments the mammal is a human.

In some preferred embodiments, the first container has a total volume of up to 500 mL and/or is provided as an injectable formulation. In other preferred embodiments, the first container may contain a % w/v of detergent greater than the % w/v of phosphatidylcholine or may contain no phosphatidylcholine. In one preferred embodiment, the present invention provides the detergent at a concentration above its critical micellar concentration (CMC). The kits may comprise a variety of pharmacologically active detergents such as, for example, a lipophilic detergent, a hydrophilic detergent, an ionic detergent, a non-ionic detergent, a glyceride, a bile salt, and a zwitterionic detergent. In a more preferred embodiment, the active detergent is a bile salt, most preferably sodium deoxycholate. A first container in the kit herein may, in some embodiments include up to 3 g detergent. In other embodiments, a first container in the kit herein may include more than 0.0002 g detergent. In any of the embodiments herein the first container may further include a second detergent.

Preferably, the first container may further comprise a second therapeutic agent such as, for example, an anti-microbial agent, a vasoconstrictor, an anti-thrombotic agent, an anti-coagulation agent, a suds-depressant, an anti-inflammatory agent, an analgesic, a dispersion agent, an anti-dispersion agent, a penetration enhancer, a steroid, a tranquilizer, a muscle relaxant, and an anti-diarrhea agent. In some embodiments the second therapeutic agent is an analgesic, anti-microbial agent, or an anti-inflammatory agent. More preferably, the second therapeutic agent is an analgesic, or most preferably lidocaine. In another embodiment, the kit provides a second container comprising the second therapeutic agent as described herein.

One embodiment of the present invention contemplates a kit herein for reducing fat deposits under the eye, chin, or arm, as well as the buttock, calf, back, thigh, ankle, or stomach of a mammal. In another embodiment, the kit may reduce specific types of fat deposits such as, for example, eyelid fat herniation, lipomas, lipodystrophy, buffalo hump lipodystrophy, diffused body fat around trunk and arms, or fat deposits associated with cellulite.

Business Methods

The methods and the kits disclosed herein can be used to perform business services and/or sell business products.

In some embodiments, the present invention contemplates a business method that sells the kits herein or provides treatment services. For example, the business can make a formulation based on the compositions described herein. The business methods herein can then manufacture kits containing such formulations and sell such kits in exchange for a fee. In some embodiments, the business method licenses a third party to manufacture the kit. In some embodiments, the business contracts a sales support to sell such kits.

The business can alternatively or in addition perform treatment services in exchange for service fees. The service can be provided directly to patients and the fee can vary depending on the length of the procedure and/or amount of active detergents used.

It is understood that there are numerous other embodiments and methods of using the present invention that will be apparent embodiments to those of ordinary skill in the art after having read and understood this specification and examples. The following examples are meant to illustrate one or more embodiments of the invention and are not meant to limit the invention to that which is described below.

EXAMPLES

Example 1

Sodium Deoxycholate and Phosphatidylcholine Formulations

Phosphatidylcholine bile salt formulation (PBF) (5.0% highly purified soy derived PC, 4.75% sodium deoxycholate, and 0.9% benzyl alcohol, in sterile water, Table 2) was obtained from Hopewell Pharmacy, Hopewell, N.J. Sodium deoxycholate and Triton X-100 detergent (Triton, alkylaryl polyether alcohol) were obtained from Sigma-Aldrich Corp. (St. Louis, Mo.). Empigen BB detergent (Empigen, lauryldimethylbetaine) was obtained from Calbiochem, Biosciences, Inc., (La Jolla, Calif.). An injectible PBF solution was made according to Table 2 below. Stock reagents (5% dilutions) were prepared in PBS buffer.

TABLE 2

| Injectable PBF | |
| --- | --- |
| Phosphatidylcholine | 5.00% (w/v) |
| Sodium deoxycholate | 4.75% |
| Benzyl alcohol | 0.90% |
| Water | 100 mL |

The molecular structure of (a) phosphatidylcholine, (b) sodium deoxycholate and (c) benzyl alcohol are depicted in FIG. 1.

Example 2

Effects of Sodium Deoxycholate and Phosphatidylcholine Solutions in Cultured Cells To measure cell viability after detergent treatment, HaCaT human keratinocyte cells were cultured in DMEM (Dulbecco's modified Eagle's medium) supplemented with 10% fetal calf serum, penicillin, and streptomycin. HaCaT cells were cultured in 6 well plates and incubated with 0, 0.005, 0.050 or 0.500% of the PBF or sodium deoxycholate for 30 min at 37° C. prior to determination of cell viability using the MTS assay, which uses a tetrazolium compound that produces a color change when bioreduced by metabolically active cells (CellTiter 96 Aqueous Non-Radioactive Cell Proliferation Assay, Promega, Corp. Madison, Wis.). Cell viability was determined by an absorbance spectrophotometer (at 490 nm) after 4 hour incubation with the assay at 37° C. To determine cell viability in fresh tissue, fat specimens were incubated for 4 hours in 24 well plates with stock reagents and the MTS assay. Tissue specimens were then visualized for color change and the amount of MTS in their supernatants was measured by absorbance (at 490 nm). All studies were performed in triplicate. Absorbance at 490 nm (OD 490) is proportional to the number of living cells in the culture. There was comparable OD 490 in the control and 0.005% dilutions of both compounds (FIG. 2a), indicating little effect of these substances on cell viability at this concentration. Cell viability progressively decreased at 0.05% and 0.5% concentrations of both solutions.

Figure 2A:
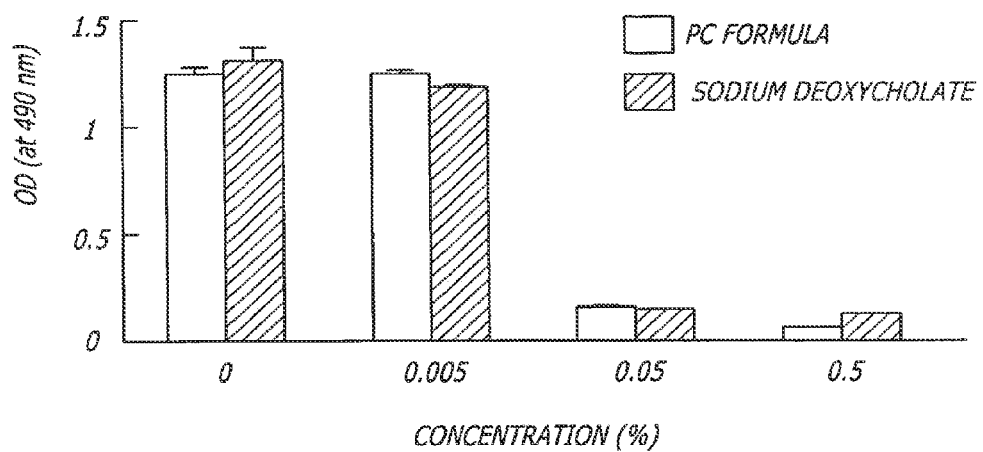
FIG. 2 depicts the effects of phosphatidylcholine bile salt formulation (PBF) (5.0% highly purified soy derived PC, 4.75% sodium deoxycholate, and 0.9% benzyl alcohol, in sterile water) and sodium deoxycholate alone on cultured cell viability according to the teachings of the present invention: (a) MTS assay measuring viability of keratinocytes exposed to the PBF and sodium deoxycholate alone; (b) lactate dehydrogenase (LDH) assay measuring LDH release by cells exposed to the PBF and sodium deoxycholate alone.
Figure 2B:
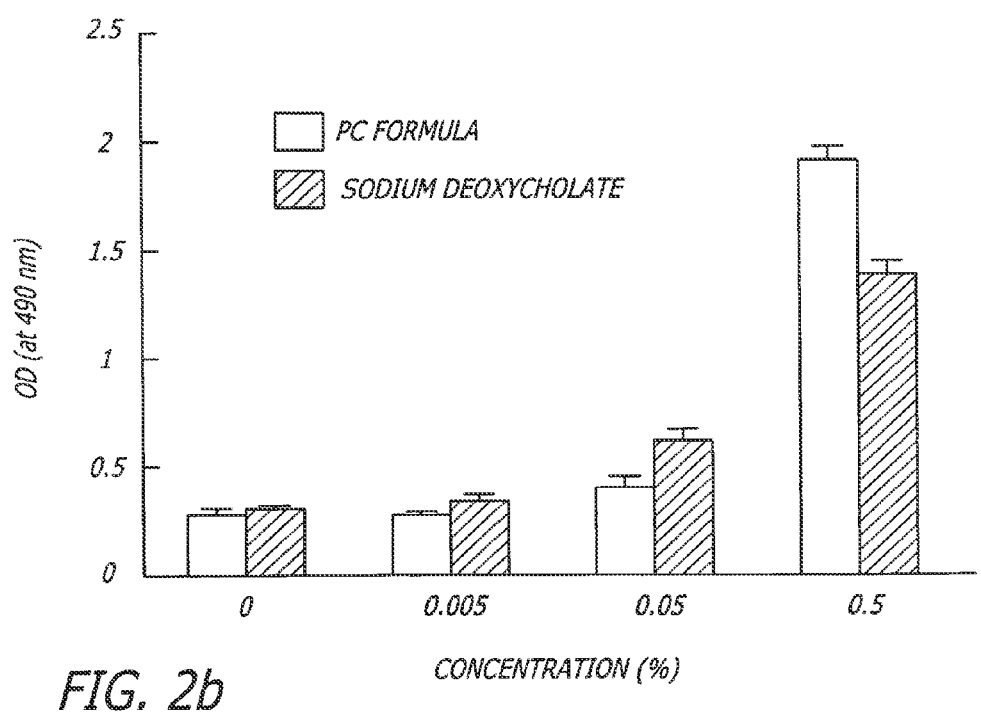

Cell lysis in response to detergent treatment was determined in HaCaT cells incubated with the reagents at the indicated cell dilutions for 30 min at 37° C. Lysis in cultured cells was measured using a lactate dehydrogenase (LDH) assay and within tissue using calcein, a fluorescent marker retained in cells with intact cell membranes. The LDH assay measures the activity of LDH, which is a cytosolic enzyme released when cells are lysed. Lactate dehydrogenase release was measured by absorbance (at 490 nm) after a 1 hour incubation with the LDH assay as recommended by the manufacturer (CytoTox 96 Non-Radioactive Cytotoxicity Assay, Promega). All studies were performed in triplicate. LDH release is directly proportional to absorbance at 490 nm (OD 490). Because penetration into intact tissues may be likely a limiting factor, cell cultures were used to determine the dilutions of the reagents (PBF and deoxycholate) necessary to affect cells. As is illustrated in FIG. 2a, sodium deoxycholate profoundly decreased the viability of cultured cells approximately equal to the complete PBF. This finding was reproduced in tissue by exposing porcine fat to PBF and deoxycholate (FIG. 3). These results support the unexpected observation that sodium deoxycholate plays a major, active role in the PBF. There was minimal LDH release from control cells and those incubated with 0.005% dilutions of both compounds (FIG. 2b). Moreover, both the PBF and deoxycholate treated cell cultures demonstrated a concentration dependent increase in cell lysis (FIG. 2b). Moreover, the direct lytic effects observed in cultured cells treated with these agents suggest activity independent of endogenous lipase. There was progressively more LDH released at 0.05% and 0.5% of the PBF and deoxycholate. Comparing the effects of the PBF to deoxycholate in cell culture led to the surprising result that deoxycholate caused similar loss of cell viability, but less cell lysis. These data unexpectedly demonstrate that deoxycholate acts as the active component in PBF.

Example 3

Effects of Sodium Deoxycholate and Phosphatidylcholine Solutions in Porcine Tissue Porcine tissue was obtained immediately after sacrifice, shaved, and placed on ice for a maximum of four hours before use. Fat specimens were obtained by removing the epidermis and dermis of a punch biopsy with a scalpel and trimmed Fat specimens were loaded with calcein dye by incubating 1 hour at 37° C. with Calcein-AM (Sigma). Stock reagents were added to the fat specimens and incubated for 30 min at 37° C. with gentle agitation. Calcein retention was determined by tissue fluorescence using purple (411 nm) light and visually observing the emitted green (500 nm) light using an emission filters.

Histology was performed by injecting stock reagent solutions (0.5 mL) into full thickness porcine skin at various levels (epidermis, dermis, and subcutaneous tissue) with 1.0 mL syringes and 30-gauge, 0.5 inch needles. Needle depth was visualized along the margin of the porcine tissue with the intent of saturating the target tissue. One hour after incubation with PBS at 37° C., multiple 5.0 mm biopsy specimens were obtained from the injected sites, each condition performed in triplicate. Tissue was fixed in formaldehyde, paraffin-embedded, and stained with hematoxylin-eosin. Specimens were evaluated by a board-certified dermatopathologist who was blinded to the treatment protocol.

Figure 3A:
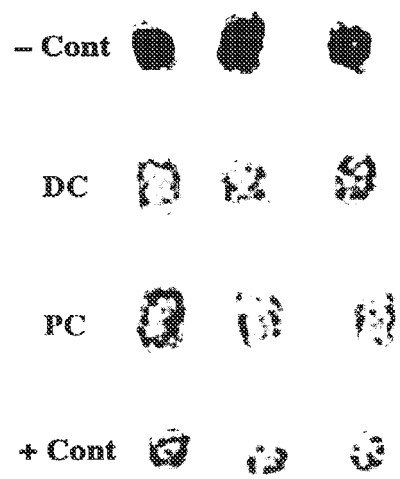
FIG. 3 depicts the effects of PBF and sodium deoxycholate alone on primary porcine fat tissue according to the teachings of the present invention: (a) MTS assay producing purple pigment, indicating living cells, in fat specimens treated with the PBS buffer as negative control (−Cont), sodium deoxycholate alone (DC), the PBF, and Triton detergent as positive control (+Cont); (b) A comparison of fat cell viability between the different treatments.
Figure 3B:
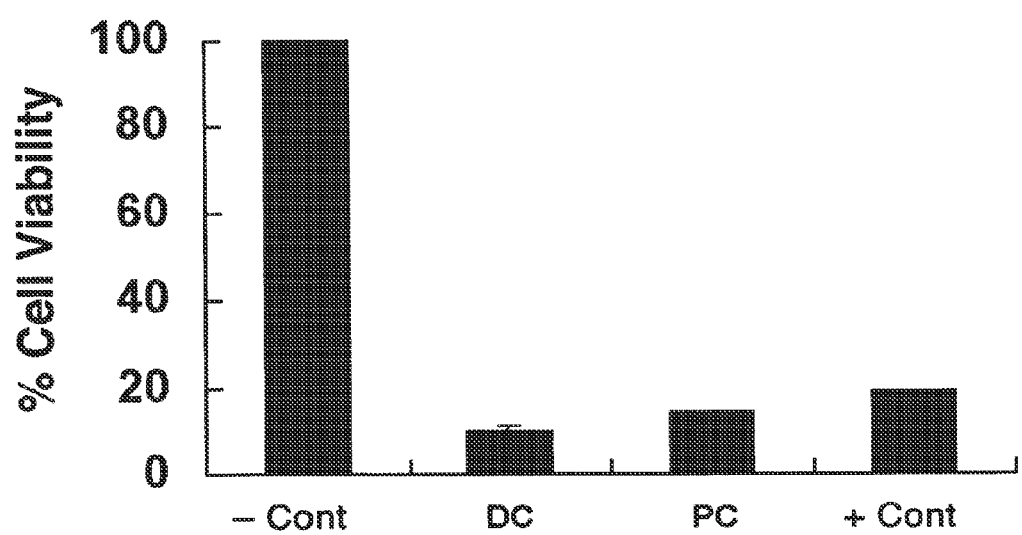

Fresh porcine skin was used to determine if the effects of these detergent substances on cultured cells were similar in tissue. FIG. 3a demonstrates the production of dark purple pigment (indicating viable cells) in fat tissue treated with the PBS buffer (negative control) using the MTS assay. The PBF and 5% solutions of deoxycholate and Triton detergent (positive control) demonstrated a comparable loss of purple dye (indicating cell death) in the treated fat specimens. The difference in fat cell viability between the solutions was quantified by measuring the absorbance (at 490) of the supernatants collected from the treated fat specimens (FIG. 3b). All reagents had significant effects on the fat cell viability of fresh tissue.

Figure 4:
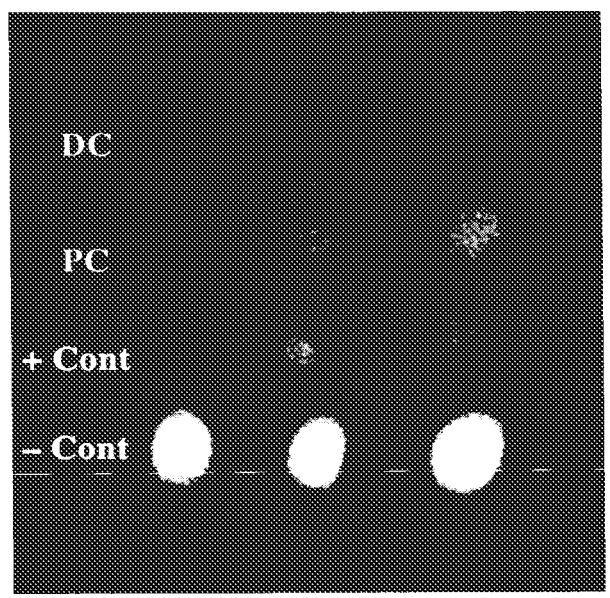
FIG. 4 depicts calcein fluorescence in fat specimens treated with sodium deoxycholate alone (DC), PBF, Triton detergent as positive control (+Cont), and PBS buffer as negative control (−Cont) according to the teachings of the present invention.
Figure 5A:
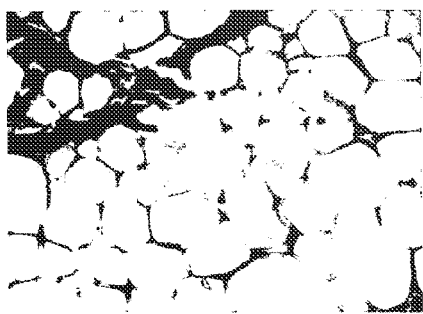
FIG. 5 depicts light microscopy of porcine skin biopsies after treatment revealing (a) control lipocytes and (b) lipocytes after PBF injection (H&E, original magnification, ×20); (c) control lipocytes and (d) lipocytes after injection of sodium deoxycholate alone (H&E, original magnification, ×10); (e) control muscle and (f) muscle after injection of phosphatidylcholine alone (H&E, original magnification, ×10); (g) fat after injection with Empigen detergent (H&E, original magnification, ×20).
Figure 5B:
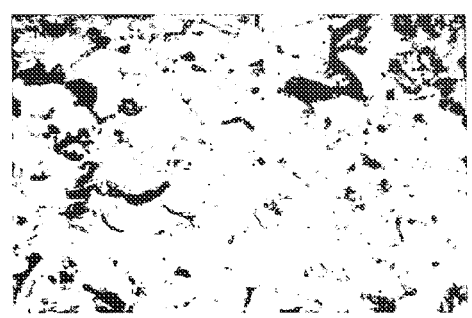
Figure 5C:
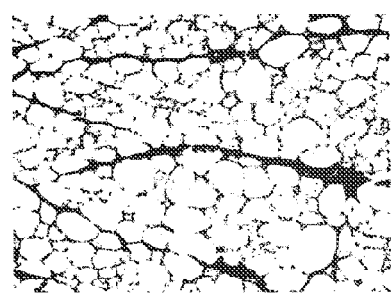
Figure 5D:
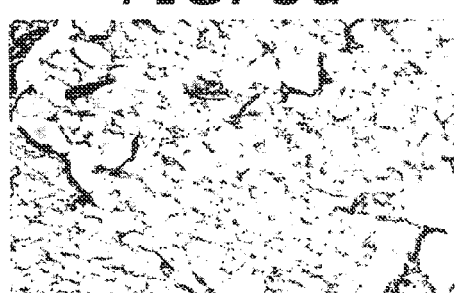
Figure 5E:
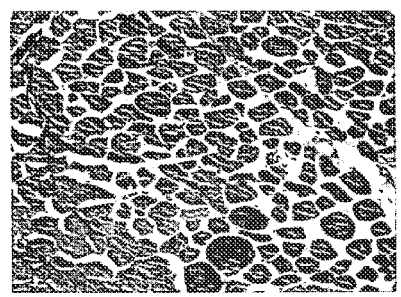
Figure 5F:
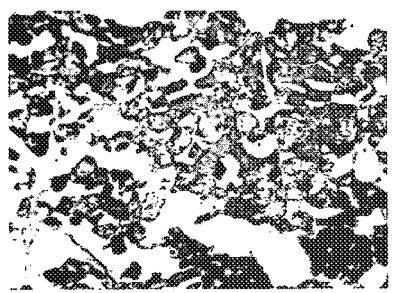
Figure 5G:
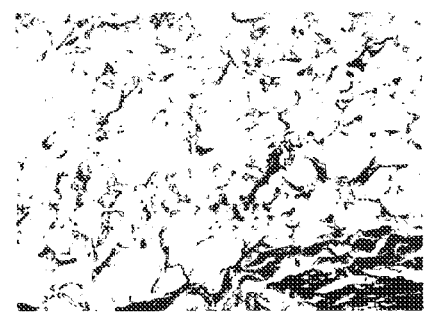

Cell lysis was confirmed using a calcein dye release assay. Calcein becomes fluorescent after hydrolysis and is retained in cells that have intact cell membranes. Because it does not label dead cells and is lost under conditions that cause cell lysis, loss of green fluorescence in fat tissue samples loaded with the dye calcein indicates cell lysis (FIG. 4). Samples treated with the deoxycholate, PBF, and Triton detergent (positive control) exhibited similar loss of fluorescence.

The histologic changes resulting from injection of PBF, deoxycholate, and Empigen, are shown in FIG. 5. Phosphatidylcholine bile salt formulation (FIG. 5b) and deoxycholate (FIG. 5d) produced histologic effects similar to those caused by Empigen (FIG. 5g) and Triton (not shown), two well-characterized laboratory detergents. These changes were apparent in both fat and muscle. Marked blurring and dissolution of adipocyte cell membranes with disruption of its normal lobular architecture were seen, after injection of both the PBF (FIG. 5b) and deoxycholate (FIG. 5d). FIG. 5f demonstrates muscle fiber disarray and atrophy after PBF injection. Similar changes in muscle tissue were visible in the specimens treated with deoxycholate and the Triton and Empigen detergents. There were no changes in the epidermis, dermis, or adnexal structures after injection of the reagents with the exception of Empigen, which caused loss of fibroblast nuclear staining and hyalinization of dermal collagen. Moreover, from clinical reports, it is apparent that a brisk inflammatory response, such as erythema and edema, occurs after injection with the detergents. Repeated inflammation can potentially lead to fibrosis, especially after multiple injections. Fibrosis has been reported in several patients who developed firm nodules at injection sites after PBF administration that eventually resolve over several months.

Histologic findings reveal that the injectable PBF and deoxycholate alone cause architectural disruption in fat and muscle, but had no apparent affect on the epidermis, dermis, or adnexae (FIG. 5). However, Empigen BB, a potent laboratory detergent, had profound histologic effects on dermal collagen (connective tissue). Alternatively, fat and muscle can be more sensitive to detergent treatment than these other structures at the tested concentrations (similar to those used in clinical practice).

Through a series of laboratory experiments utilizing fresh tissue specimens and cell cultures, it has been demonstrated that the PBF popularly used in subcutaneous injections for fat dissolution works primarily by causing non-specific lysis of cell membranes. Cell membranes are constituents of all tissue types; specifically, the present inventor demonstrated that these detergents cause solubilization of fat, muscle and connective tissue. Therefore sodium deoxycholate, the bile salt component of the formula used to dissolve the phosphatidylcholine, was the major active ingredient of these prior art formulations. This conclusion is supported by the fact that pharmacologically active detergents, such as bile salts are potent solubilizers of cell membranes.

Example 4

Clinical Experience with Sodium Deoxycholate Compositions

Figure 6A:
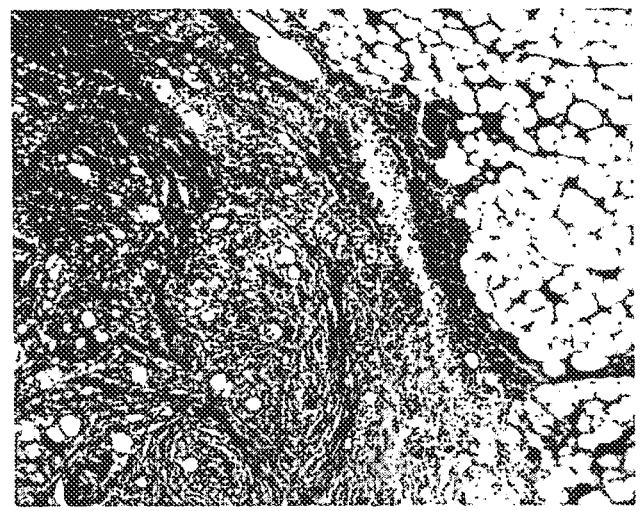
FIG. 6 depicts a lipoma removed from a patient two days after injection with deoxycholate according to the teachings of the present invention: (a) gross pathology and (b) histology (H&E, original magnification, ×20).
Figure 6B:
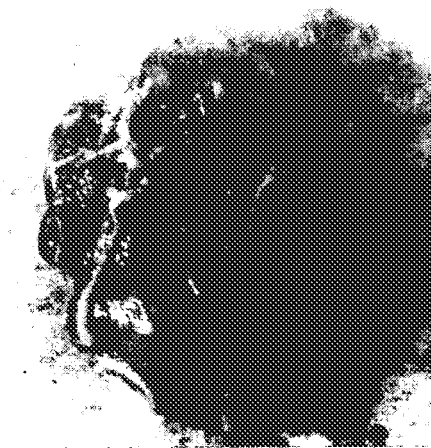

Patients having lipomas, benign, isolated collections of adipose tissue, were injected with sodium deoxycholate (DC) solutions without phosphatidylcholine directly into the lipoma. The results of this study demonstrate that the detergent effects of deoxycholate seen on fat in animal tissues are reproducible clinically in humans. All injected lipomas were reduced in size after at least one treatment with varied concentrations of deoxycholate (Table 3). A lipoma from one patient, injected with 1% DC, was excised after treatment and pathological and histological analysis performed. Within the excised lipoma, necrosis is visible grossly (FIG. 6a) with a well demarcated area of hemorrhage and necrosis on the lateral edge extending into the middle of the lipoma fat which contrasts with the normal lipoma fat which is lighter in color. Histological analysis (FIG. 6b) reveals a well defined area of hemorrhage and necrotic fat as well as a significant inflammatory reaction which contrasts to the adjacent normal round clear fat cells.

TABLE 3

Reduction in size of lipomas after DC treatment

| Lipoma | Size (cm) Pre-treatment | Size (cm) Post-treatment | Total Treatments (% DC injected) |
|---|---|---|---|
| 1 | 2.00 × 1.00 | 1.25 × 0.50 | 2 (2.5%) |
| 2 | 2.00 | 1.50 × 0.50 | 3 (5% and 2.5%) |
| 3 | 2.00 × 2.50 | 2.00 × 1.00 | 3 (5% and 2.5%) |
| 4 | 4.00 × 1.75 | 2.50 × 2.00 | 2 (1%) |
| 5 | 2.00 × 1.75 | 1.25 | 2 (1%) |
| 6 | 2.80 | 0.50 | 1 (5%) |
| 7 | 1.00 | Imperceptible | 1 (1%) |

Example 5

Treatment of Lipodystrohy in a HIV Patient with Sodium Deoxycholate Compositions An HIV lipodystrophy patient with symmetrical fat deposits in his face just ventral of his master muscle (sort of in his cheeks, like acorns in the mouth of a chipmunk) was injected with 1% deoxycholate. At 1 month follow up, there was a 50% apparent reduction in deposit volume on both sides. The results of this study demonstrate that the effects of deoxycholate seen on fat in animal tissues are reproducible clinically in humans.

Example 6

Effects of Sodium Deoxycholate and Sodium Deoxycholate-Phosphatidylcholine Solutions on Melanocytes Melanocytes in melanocyte media on a 96-well dish were differentiated at 37° C. in a humidified, 5% $CO_2$ incubator for a week. Media was aspirated and washed with 1×PBS once. Cells were treated with different concentrations of DC (from 0 to 0.5%) with or without 1% PC in 1×PBS. Each treatment was done in triplicates (Table 4). The plates were incubated at 37° C. in a humidified, 5% $CO_2$ incubator for 30 min. The incubated plates were aspirated and washed with 1×PBS. 10 mL of MTS (3-(4,5-dimethyl-2-yl)-5-(3-carboxymethoxyphenyl)-2-(4-sulfophenyl)-2H-tetrazolium, inner salt) assay solution was prepared (mixed 40 uL MTS (Promega, Madison Wis.) per MeI 1×PBS). 100 ul of MTS solution was added to each well of the plates. The plates were incubated at 37° C. incubator (non-hunified) for 120 min. OD was taken with spectrophotometer at 490 nm.

Figure 7:
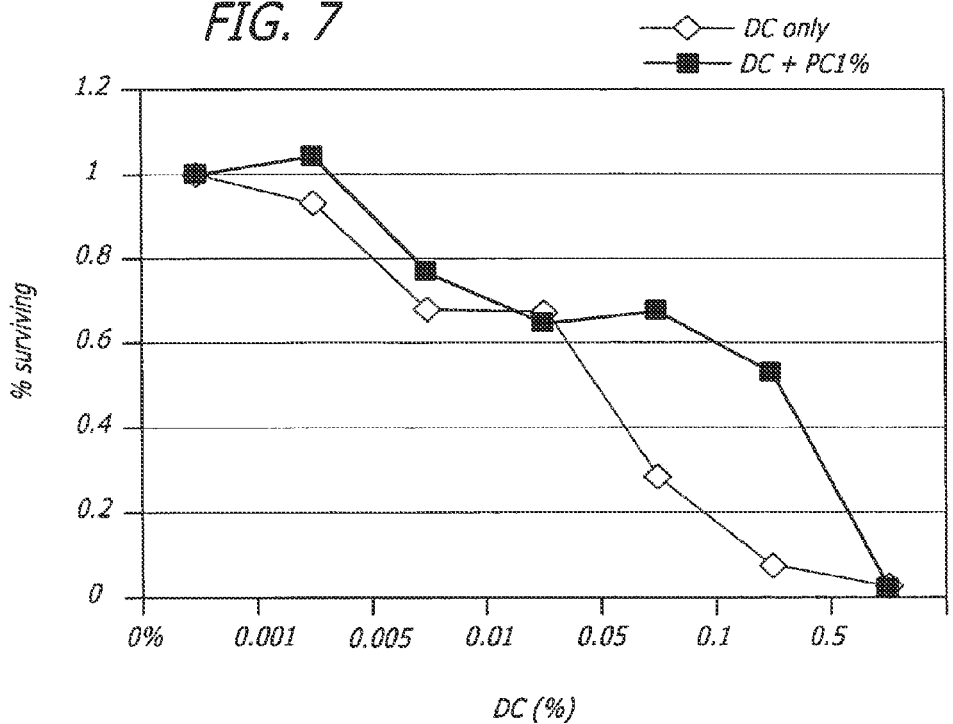
FIG. 7 depicts effects of sodium deoxycholate only and sodium deoxycholate-1% phosphatidylcholine solutions on melanocytes.

FIG. 7 illustrates the survival of melanocytes in sodium deoxycholate solution and sodium deoxycholate with 1% phosphatidylcholine solution. A375P is a melanoma cell line (P represents poorly metastatic). On y-axis, 1 represents 100% survival when no DC is added. All % concentrations are w/v %. LD50 (concentration at which 50% of the fat cells are dead) of only sodium deoxycholate solution for melanocyte cell line was found to be around 0.04% sodium deoxycholate. The addition of sodium deoxycholate with 1% phosphatidylcholine solution increases the LD50 by ~5-6 fold.

Results of this study demonstrate that addition of 1% phosphatidylcholine inhibits apoptosis in vitro i.e., the presence of PC makes it 5-times harder for DC to kill the melanocytes, showing that PC detracts from, and thus does not enhance the cell killing power of DC.

TABLE 4

Melanocytes after treatment with DC only and DC + 1% PC

| DC | Melanocytes surviving in DC only | Average | Percentage surviving % | Melanocytes surviving in DC + 1% PC | Average | Percentage surviving % |
|---|---|---|---|---|---|---|
| 0% | 0.163 | 0.166667 | 1 | 0.283 | 0.342333 | 1 |
|  | 0.16 |  |  | 0.326 |  |  |
|  | 0.177 |  |  | 0.418 |  |  |
| 0.001 | 0.158 | 0.155333 | 0.932 | 0.248 | 0.356333 | 1.040896 |
|  | 0.148 |  |  | 0.239 |  |  |
|  | 0.16 |  |  | 0.582 |  |  |
| 0.005 | 0.128 | 0.113333 | 0.68 | 0.226 | 0.263667 | 0.770204 |
|  | 0.109 |  |  | 0.259 |  |  |
|  | 0.103 |  |  | 0.306 |  |  |
| 0.01 | 0.124 | 0.112333 | 0.674 | 0.197 | 0.220667 | 0.644596 |
|  | 0.107 |  |  | 0.223 |  |  |
|  | 0.106 |  |  | 0.242 |  |  |

TABLE 4-continued

Melanocytes after treatment with DC only and DC + 1% PC

| DC | Melanocytes surviving in DC only | Average | Percentage surviving % | Melanocytes surviving in DC + 1% PC | Average | Percentage surviving % |
|---|---|---|---|---|---|---|
| 0.05 | 0.056 | 0.047333 | 0.284 | 0.207 | 0.232 | 0.677702 |
|  | 0.038 |  |  | 0.214 |  |  |
|  | 0.048 |  |  | 0.275 |  |  |
| 0.1 | 0.009 | 0.013 | 0.078 | 0.191 | 0.182333 | 0.532619 |
|  | 0.014 |  |  | 0.168 |  |  |
|  | 0.016 |  |  | 0.188 |  |  |
| 0.5 | 0.001 | 0.004 | 0.024 | 0.012 | 0.006333 | 0.0185 |
|  | 0.009 |  |  | 0.003 |  |  |
|  | 0.002 |  |  | 0.004 |  |  |

Example 7

Effects of Sodium Deoxycholate and Sodium Deoxycholate-Phosphatidylcholine Solutions on Adipocytes Adipocytes in adipocyte media on a 96-well dish were differentiated at 37° C. in a humidified, 5% $CO_2$ incubator for a week. Media was aspirated and washed with 1×PBS once. Cells were treated with different concentrations of DC (from 0 to 0.5%) with or without 1% PC in 1×PBS. Each treatment was done in triplicates (Table 5). The plates were incubated at 37° C. in a humidified, 5% $CO_2$ incubator for 30 min. The incubated plates were aspirated and washed with 1×PBS.

10 mL of MTS (3-(4,5-dimethyl-2-yl)-5-(3-carboxymethoxyphenyl)-2-(4-sulfophenyl)-2H-tetrazolium, inner salt) assay solution was prepared (mixed 40 uL MTS (Promega, Madison Wis.) per 1 mL 1×PBS). 100 ul of MTS solution was added to each well of the plates. The plates were incubated at 37° C. incubator (non-humidified) for 120 min. OD was taken with spectrophotometer at 490 nm.

Figure 8:
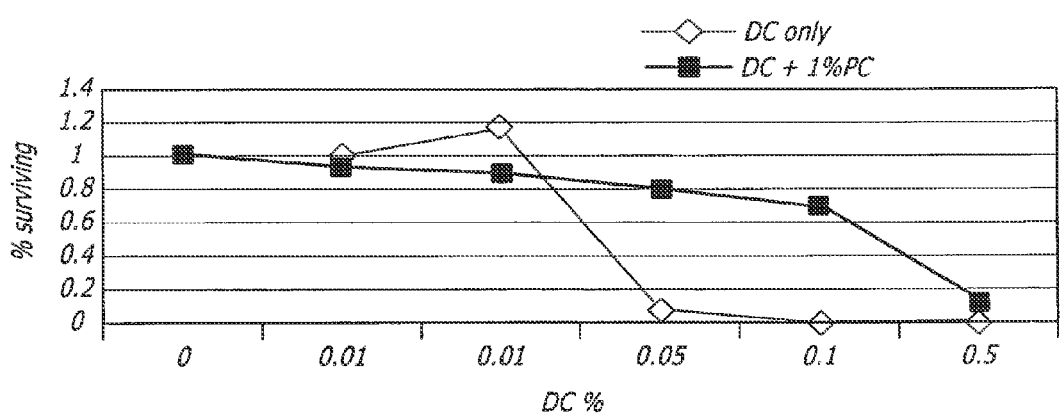
FIG. 8 depicts effects of sodium deoxycholate only and sodium deoxycholate-1% phosphatidylcholine solutions on adipocytes.

FIG. 8 illustrates the survival of adipocytes in sodium deoxycholate solution and sodium deoxycholate with 1% phosphatidylcholine solution. The adipocyte cells are primary (i.e., taken freshly from a person) adipocytes, cultured in vitro to maturity before treatment with DC. On y-axis, 1 represents 100% survival when no DC is added. All % concentrations are w/v %. LD50 (concentration at which 50% of the fat cells are dead) of only sodium deoxycholate solution for adipoocyte cell line was found to be around 0.02% sodium deoxycholate. The addition of sodium deoxycholate with 1% phosphatidylcholine solution increases the LD50 by ~5-6 fold.

Results of this study demonstrate that addition of 1% phosphatidylcholine inhibits apoptosis in vitro i.e., the presence of PC makes it 5-times harder for DC to kill the adipocytes, showing that PC detracts from, and thus does not enhance the fat cell killing power of DC.

TABLE 5

Adipocytes after treatment with DC only and DC + 1% PC

| DC | Adipocytes surviving in DC only | Average | Percentage surviving % | Adipocytes surviving in DC + 1% PC | Average | Percentage surviving % |
|---|---|---|---|---|---|---|
| 0% | 0.036 | 0.113 | 1 | 0.191 | 0.200 | 1 |
|  | 0.112 |  |  | 0.19 |  |  |
|  | 0.114 |  |  | 0.22 |  |  |
| 0.005 | 0.52 | 0.111 | 0.982 | 0.195 | 0.186 | 0.930 |
|  | 0.105 |  |  | 0.178 |  |  |
|  | 0.117 |  |  | 0.186 |  |  |
| 0.01 | 0.067 | 0.131 | 1.163 | 0.174 | 0.178 | 0.891 |
|  | 0.133 |  |  | 0.183 |  |  |
|  | 0.13 |  |  | 0.179 |  |  |
| 0.05 | 0.01 | 0.09 | 0.079 | 0.167 | 0.159 | 0.795 |
|  | 0.009 |  |  | 0.164 |  |  |
|  | 0.008 |  |  | 0.147 |  |  |
| 0.1 | 0 | 0 | 0 | 0.138 | 0.141 | 0.707 |
|  | 0 |  |  | 0.14 |  |  |
|  | 0 |  |  | 0.147 |  |  |
| 0.5 | 0 | 0 | 0 | 0.032 | 0.024 | 0.123 |
|  | 0 |  |  | 0.02 |  |  |
|  | 0 |  |  | 0.022 |  |  |

Example 8

Effects of Addition of Phosphatidylcholine to 4.75% Sodium Deoxycholate Solutions on Viable Adipocytes FIG. 9 illustrates survival of adipocytes when phosphatidylcholine is added to 4.75% sodium deoxycholate solution. On y-axis, 1 represents 100% survival. All % concentrations are w/v %. Survival of the cells in the absence of DC and PC is on an average 0.113.

Results of this study demonstrate that addition of phosphatidylcholine to sodium deoxycholate solution does not necessarily contribute to adipolysis in vitro, as deoxycholate is both necessary and sufficient to mediate 100% adipolysis of cultured adipocytes. Furthermore, a close examination of these data (Table 6) shows that 5% phosphatidylcholine actually inhibits adipolysis slightly, which is not surprising in the light of the 5-6 fold increase in LD50 conferred by the addition of phosphatidylcholine (as demonstrated in example 7). These data collectively support the notion that sodium deoxycholate is an active ingredient for adipolysis, and that phosphatidylcholine is not only unnecessary, but actually inhibits fat removal.

TABLE 6

Adipocytes after addition of PC to 4.75% DC

| PC | Adipocytes surviving by adding PC to 4.75% DC | Average | Percentage surviving % |
|---|---|---|---|
| 0 | 0 | 0 | 0 |
|  | 0 |  |  |
|  | 0 |  |  |
| 0.01 | 0 | 0 | 0 |
|  | 0 |  |  |
|  | 0 |  |  |
| 0.1 | 0 | 0 | 0 |
|  | 0 |  |  |
|  | 0 | 0 | 0 |
| 1 | 0 | 0 | 0 |
|  | 0 |  |  |
|  | 0 |  |  |
| 5 | 0.002 | 0.009 | 0.079 |
|  | 0.013 |  |  |
|  | 0.012 |  |  |

Example 9

Inhibition of Adipolysis by Pre-Incubation with Human Lipoma Fat

The experiment was performed on a series of immortalized melanocyte cell lines. Resected human lipomas were ground up, and DC-containing media was mixed with the human fat and agitated for 24 hours. The material was centrifuged to pellet insoluble contents. The supernatants were then added on top of cultured melanocytes. Control was the identical DC-containing media not exposed to the fat chunks. Also, fat alone (no media) was added as a control.

FIG. 10 shows that pre-incubation of 0.1% DC with the fat (Table 7) appears to reduce killing. It could be by releasing some form of inhibitor (e.g., example 7 shows that PC inhibits DC killing in vitro) or could be by retaining the DC in the fat pellet that was spun out in the centrifuge. But it is evident in this experiment that the presence of the fat limits the killing properties of DC, may be by direct inhibition (like PC) or by sequestration (i.e., into the fat pellet). This can further explain the observation that injection of DC into fat spares the surrounding tissues.

TABLE 7

Inhibition of adipolysis by pre-incubation with human lipoma fat

|  | Control | | | DC 0.1% | | | DC 0.1% + fat | | | Fat | | |
|---|---|---|---|---|---|---|---|---|---|---|---|---|
| A375M | 0.598 | 0.602 | 0.616 | 0.066 | 0.063 | 0.063 | 0.456 | 0.382 | 0.365 | 0.494 | 0.517 | 0.601 |
| Actual | 0.598 | 0.602 | 0.616 | 0.066 | 0.063 | 0.063 | 0.456 | 0.382 | 0.365 | 0.494 | 0.517 | 0.601 |
| Average |  |  | 0.605 |  |  | 0.064 |  |  | 0.401 |  |  | 0.537 |
| Percentage |  |  | 1.000 |  |  | 0.106 |  |  | 0.662 |  |  | 0.888 |
| CHL | 0.63 | 0.683 | 0.663 | 0.064 | 0.066 | 0.064 | 0.402 | 0.426 | 0.378 | 0.612 | 0.623 | 0.646 |
| Actual | 0.63 | 0.683 | 0.663 | 0.064 | 0.066 | 0.064 | 0.402 | 0.426 | 0.378 | 0.612 | 0.623 | 0.646 |
| Average |  |  | 0.659 |  |  | 0.065 |  |  | 0.402 |  |  | 0.627 |
| Percentage |  |  | 1 |  |  | 0.098 |  |  | 0.610 |  |  | 0.952 |
| WM266 | 0.548 | 0.56 | 0.567 | 0.07 | 0.061 | 0.058 | 0.281 | 0.308 | 0.314 | 0.48 | 0.507 | 0.533 |
| Actual | 0.548 | 0.56 | 0.567 | 0.07 | 0.061 | 0.058 | 0.281 | 0.308 | 0.314 | 0.48 | 0.507 | 0.533 |
| Average |  |  | 0.558 |  |  | 0.063 |  |  | 0.301 |  |  | 0.507 |
| Percentage |  |  | 1.000 |  |  | 0.113 |  |  | 0.539 |  |  | 0.907 |
| SKmel28 | 0.583 | 0.643 | 0.620 | 0.061 | 0.060 | 0.060 | 0.290 | 0.304 | 0.302 | 0.569 | 0.591 | 0.616 |
| Actual | 0.583 | 0.643 | 0.620 | 0.061 | 0.060 | 0.060 | 0.290 | 0.304 | 0.302 | 0.569 | 0.591 | 0.616 |
| Average |  |  | 0.615 |  |  | 0.060 |  |  | 0.299 |  |  | 0.592 |
| Percentage |  |  | 1.000 |  |  | 0.098 |  |  | 0.485 |  |  | 0.962 |
| Blank | 0.052 | 0.052 | 0.052 | 0.052 | 0.052 | 0.052 | 0.052 | 0.052 | 0.052 | 0.052 | 0.052 | 0.052 |

Example 10

Human Lipoma Studies with Sodium Deoxycholate Compositions

Six patients having 12 lipomas were injected with sodium deoxycholate (DC) solutions over a period of six months. All injected lipomas reduced in size after at least one treatment (Table 8). Measurements were made by physical measurements and ultrasound imaging. The results of this study demonstrate that the detergent effects of deoxycholate seen on fat in animal tissues are reproducible clinically in humans and that there is a significant reduction in the size of lipomas after the treatment.

Table 8

Human lipoma studies with sodium deoxycholate compositions

| Lipoma | Pre-treatment size (cm) | Post-treatment size | Change in volume (%) | Total Treatments |
|---|---|---|---|---|
| 1 | 1 | 0 | −100% | 1 |
| 2 | 2 | 1.0, 0.3, 0.5 | n/a | 3 |
| 3 | 2 × 2.5 | 1 × 1.5 | 84% | 3 |
| 4 | 4 × 3.5 | 2 | 84% | 4 |
| 5 | 2 × 1.8 | 1.3 | 92% | 4 |
| 6 | 2.8 | 0.5 | 99% | 1 |
| 7 | 3 × 2 | 0.8 | 97% | 2 |
| 8 | 1 | 0 | 100% | 2 |
| 9 | 2 × 1 | 1.2 × 0.8 | 67% | 2 |
| 10 | 2 | 1.3 | 73% | 2 |
| 11 | 2 | 1.4 × 1 | 79% | 1 |
| 12 | 1 | 0.8 | 50% | 1 |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values Size (cm) set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for treating a benign, isolated collection of adipose tissue which method comprises injection of an effective amount of a composition comprising deoxycholate in the absence of phosphatidylcholine into the tissue under conditions wherein the size of said tissue is reduced.

2. A method for treating a lipoma which method comprises injection of an effective amount of a composition comprising deoxycholate in the absence of phosphatidylcholine into the lipoma under conditions wherein the size of said lipoma is reduced.

3. The method of claim 1, wherein said deoxycholate composition is administered as a solution.

4. The method of claim 3, wherein said solution comprises a concentration of deoxycholate of from 1 to 5 percent.

5. The method of claim 3, wherein said solution comprises a concentration of deoxycholate is 1 percent.

6. The method of claim 1, wherein said composition is administered to the patient more than once.

7. The method of claim 1, wherein said deoxycholate is sodium deoxycholate.

* * * * *